United States Patent
Wang et al.

(10) Patent No.: US 10,364,452 B2
(45) Date of Patent: Jul. 30, 2019

(54) STRIP-BASED ELECTROCHEMICAL SENSORS FOR QUANTITATIVE ANALYSIS OF ANALYTES

(71) Applicants: The Regents of the University of California, Oakland, CA (US); Electrozyme, LLC, La Jolla, CA (US)

(72) Inventors: Joseph Wang, San Diego, CA (US); Irene Litvan, La Jolla, CA (US); Joshua Ray Windmiller, Del Mar, CA (US)

(73) Assignees: The Regents of the University of California, Oakland, CA (US); Biolinq Incorporated, La Jolla, CA (US)

(*) Notice: Subject to any disclaimer, the term of this patent is extended or adjusted under 35 U.S.C. 154(b) by 226 days.

(21) Appl. No.: 15/312,733

(22) PCT Filed: Jun. 1, 2015

(86) PCT No.: PCT/US2015/033621
§ 371 (c)(1),
(2) Date: Nov. 21, 2016

(87) PCT Pub. No.: WO2015/184465
PCT Pub. Date: Dec. 3, 2015

(65) Prior Publication Data
US 2017/0226557 A1 Aug. 10, 2017

Related U.S. Application Data

(60) Provisional application No. 62/005,915, filed on May 30, 2014.

(51) Int. Cl.
*G01N 27/327* (2006.01)
*C12Q 1/00* (2006.01)
(Continued)

(52) U.S. Cl.
CPC ........... *C12Q 1/005* (2013.01); *C12Q 1/26* (2013.01); *G01N 27/3272* (2013.01);
(Continued)

(58) Field of Classification Search
CPC ............ G01N 27/327; G01N 27/3272; G01N 27/3278
See application file for complete search history.

(56) References Cited

U.S. PATENT DOCUMENTS 5,082,550 A  1/1992 Rishpon et al.
5,682,043 A  10/1997 Pei et al.
(Continued)

FOREIGN PATENT DOCUMENTS

WO  2013/179293 A1  12/2013
WO  2014/025430 A2  2/2014

OTHER PUBLICATIONS

Shirsat et al., "Amperometric Glucose Biosenor on Layer by Layer Assembled Carbon Nanotube and Polypyrrole Multilayer Film," Electroanalysis 20, 2008, No. 2, 150-156 (Year: 2008).*
(Continued)

*Primary Examiner* — Alexander S Noguerola
(74) *Attorney, Agent, or Firm* — Perkins Coie LLP

(57) ABSTRACT

Methods, systems, and devices are disclosed for providing test strip electrochemical sensors for rapid quantitative analysis of analytes in physiological fluids. In one aspect, an electrochemical sensor includes a substrate; an electrode contingent including a first electrode having a coating of carbon nanotubes (CNTs) and a second electrode on the substrate; and an entrapment layer formed on the first electrode to attach an enzymatic substance capable of causing a redox reaction in the presence of a target analyte of a fluid sample which produces a redox-active product, in which the entrapment layer is structured to include a con-
(Continued)

ductive polymer film that is reversibly dopable to conduct charge carriers across the entrapment layer and at the first electrode. For example, the electrochemical sensor can be provided on a disposable test strip to quantify L-DOPA levels in whole blood, plasma, or serum samples.

33 Claims, 10 Drawing Sheets

(51) Int. Cl.
    *C12Q 1/26*     (2006.01)
    *G01N 33/543*     (2006.01)
(52) U.S. Cl.
    CPC ..... *G01N 27/3273* (2013.01); *G01N 27/3278* (2013.01); *G01N 33/5438* (2013.01)

(56) References Cited

U.S. PATENT DOCUMENTS

| | | | |
|---|---|---|---|
| 7,399,400 B2 | 7/2008 | Soundarrajan et al. | |
| 7,943,034 B2* | 5/2011 | Diamond | G01N 27/3273 204/403.02 |
| 2003/0077515 A1 | 4/2003 | Chen et al. | |
| 2003/0201177 A1 | 10/2003 | Hodges et al. | |
| 2004/0199409 A1* | 10/2004 | Brown | A61B 5/150854 705/3 |
| 2005/0230252 A1* | 10/2005 | Tsai | C12Q 1/006 204/450 |
| 2009/0061451 A1 | 3/2009 | Achim et al. | |
| 2009/0130698 A1 | 5/2009 | Worden et al. | |

OTHER PUBLICATIONS

Wikipedia article entitled Stainless Steels downloaded Nov. 16, 2018. (Year: 2018).*
Apetrei et al., "Amperometric tyrosinase based biosensor using an electropolymerized phosphate-doped polypyrrole film as an immobilization support. Application for detection of phenolic compounds," Electrochimica Acta 56 (2011) 8919-8925 (Year: 2011).*
Seventeen pages from Mutharasan et al., "Engineering Biotechnology", Gateway Coalition—Drexel University, 2000 (note that the pages of the document are not numbered) (Year: 2000) http://www.gatewaycoalition.org/files/Engineering%20Biotechnology.pdf.*
Malone et al., Freeform Fabrication of Electroactive Polymer Actuators and Electrochemical Devices, Solid Freeform Fabrication Symposium, Proceedings of the 15th, Austin Texas 2004, pp. 697-707. (Year: 2004).*
Schaafsma, et al., "Characterization of freezing of gait subtypes and the response of each to levodopa in Parkinson's disease," Eur. J. Neurol. 2003, 10, 391.
Schrag, et al., "Depression rating scales in Parkinson's disease: critique and recommendations," Mov. Disord. 2007, 22, 1077.
Shahrokhian, et al., "Electrochemical determination of L-dopa in the presence of ascorbic acid on the surface of the glassy carbon electrode modified by a bilayer of multi-walled carbon nanotube and poly-pyrrole doped with tiron," J. Electroanal. Chem. 2009, 636, 40.
Sivanesan, et al., "Determination of L-dopa using electropolymerized 3,3',3",3'"—tetraaminophthalocyanatonickel (II) film on glassy carbon electrode," Biosens. Bioelectron. 2007, 23, 708.
Teixeira, et al., "An electrochemical sensor for L-dopa based on oxovanadium-salen thin film electrode applied flow injection system," Sensor. Actuat. B-Chem. 2007, 122, 549.
Tembe, et al., "Development of electrochemical biosensor based on tyrosinase immobilized in composite biopolymeric film," Anal. Biochem. 2006, 349, 72.
Tse, W., "Optimizing pharmacotherapy: strategies to manage the wearing-off phenomenon," J. Am.

Viswanathan, et al., "Rapid analysis of l-dopa in urine samples using gold nanoelectrode ensembles," Talanta 2007, 74, 229.
Wade, et al., "Synthetic amino acids and the nature of L-DOPA transport at the blood-brain barrier," J. Neurochem. 2006, 25, 837.
Wang, J., "Electrochemical glucose biosensors," Chem. Rev. 2008, 108, 814.
Weinzimer, et al., "Fully automated closed-loop insulin delivery versus semiautomated hybrid control in pediatric patients with type 1 diabetes using an artificial pancreas," Diabetes Care 2008, 31, 934.
Wilkins, E S., "Towards implantable glucose sensors: A review," J. Biomed. Eng. 1989, 11, 354. [24].
Wilson, et al., "Enzyme-based biosensors for in-vivo measurements," Chem. Rev. 2000, 100, 2693.
Windmiller, et al., "Bioelectronic system for the control and readout of enzyme logic gates," Sensor. Actuat. B-Chem. 2011, 155, 206.
Windmiller, et al., "Boolean-format biocatalytic processing of enzyme biomarkers for the diagnosis of soft tissue injury," Sensor. Actuat. B-Chem. 2010, 150, 285.
Yan, et al., "Electrochemical behavior of l-dopa at single-wall carbon nanotube-modified glassy carbon electrodes," J. Electroanal. Chem. 2004, 569, 47-52.
Yao, et al., "Electron-transfer properties of different carbon nanotubematerials, and their use in glucose biosensors", Anal BioanalChem (2007) 387.
International Search Report and Written Opinion of International Application No. PCT/US2015/033621; dated Oct. 8, 2015, 14 pages.
"Guidance for industry—Bioanalytical method validation," U.S. Department of Health and Human Services—Food and Drug Administration, Center for Drug Evaluation and Research (CDER): May 2001.
Albareda-Sirvent, et al., "Configurations used in the design of screen-printed enzymatic biosensors. A review," Sensor. Actuat. B-Chem. 2000, 69, 153.
Babaei, et al., "Highly sensitive simultaneous determination of L-dopa and paracetamol using a glassy carbon electrode modified with a composite of nickel hydroxide nanoparticles/multi-walled carbon nanotubes," J. Electroanal. Chem. 2013, 698, 45.
Babaei, et al., "Multi-walled carbon nanotubes/chitosan polymer composite modified glassy carbon electrode for sensitive simultaneous determination of levodopa and morphine," Anal. Methods 2011, 3, 2400.
Bandodkar, et al., "Epidermal tattoo potentiometric sodium sensors with wireless signal transduction for continuous non-invasive sweat monitoring," Biosens. Bioelectron. 2014, 54, 603.
Bergamini, et al, "A disposable electrochemical sensor for the rapid determination of levodopa," J. Pharmaceut. Biomed. 2005, 39, 54-59.
Bogdanov, et al., "Metabolomic profiling to develop blood biomarkers for Parkinson's disease," Brain 2008, 131, 389.
Rishpon, et al., "Amperometric Glucose Sensors Based on Glucose Oxidase Immobilized in Nafion", Electroanalysis, 6 (1994) 17-21.
Chou, et al., "Parkinson Study Group Cognitive/Psychiatric Working Group: A recommended scale for cognitive screening in clinical trials of Parkinson's disease," Mov. Disord. 2010, 25, 2501.
Chuang, et al., "High-fidelity determination of security threats via a Boolean biocatalytic cascade," Chem. Commun. 2011, 47, 3087.
Contin, et al., "Effect of meal timing on the kinetic-dynamic profile of levodopa/carbidopa controlled is release in parkinsonian patients," Eur. J. Clin. Pharmacol. 1998, 54, 303.
Dempsey, et al., "Development of a biosensor for endocrine disrupting compounds based on tyrosinase entrapped within a poly(thionine) film", Biosens Bioelectron 20 (2004) 367-377.
Ebisch, R., "Bluetooth® enabled medical devices: A growing market," Bluetooth SIG, Inc.: 2013.
Fahn, et al., "Levodopa and the progression of Parkinson's disease," N. Engl. J. Med. 2004, 351, 2498.
Foster, et al., "The two faces of L-DOPA: benefits and adverse side effects in the treatment of Encephalitis lethargica, Parkinson's disease, multiple sclerosis and amyotrophic lateral sclerosis", Medical Hypotheses (2004) 62, 177-181.

(56) References Cited

OTHER PUBLICATIONS

Goetz, et al., "Teaching program for the Movement Disorder Society-sponsored revision of the Unified Parkinson's Disease Rating Scale: (MDS-UPDRS)," Mov. Disord. 2010, 25, 1190.

Goodwin, et al., "L-DOPA, catecholamines, and behavior: a clinical and biochemical study in depressed patients," Biol. Psychiat. 1970, 2, 341.

Guinovart, et al., "A potentiometric tattoo sensor for monitoring ammonium in sweat," Analyst 2013, 138, 7031.

Guinovart, et al., "A reference electrode based on polyvinyl butyral (PVB) polymer for decentralized chemical measurements," Anal. Chim. Acta 2014 (accepted).

Harrison, et al., "Characterization of Perfluorosulfonic Acid Polymer Coated Enzyme Electrodes and a Miniaturized Integrated Potentiostat for Glucose Analysis in Whole Blood", Anal. Chem. 1988, 60, 2002-2007.

Hart, et al., "Screen-printed voltammetric and amperometric electrochemical sensors for decentralized testing," Electroanal. 1994, 6, 617.

Hart, et al., "Some recent designs and developments of screen-printed carbon electrochemical sensors/biosensors for biomedical, environmental, and industrial analyses," Anal. Lett. 2005, 37, 789.

Hart, J.P., "Recent developments in the design and application of screen-printed electrochemical sensors for biomedical, environmental and industrial analyses," TrAC-Trend. Anal. Chem. 1997, 16, 89.

Riggin, et al., "Liquid Chromatographic Method for Monitoring Therapeutic Concentrations of L-Dopa and Dopamine in Serum", Clin. Chem. 22, 782-784 (1976).

Henry, C., "Getting under the skin: Implantable glucose sensors," Anal. Chem. 1998, 70, 594A.

Hu, et al., "Selective determination of L-dopa in the presence of uric acid and ascorbic acid at a gold nanoparticle self-assembled carbon nanotube-modified pyrolytic graphite electrode," Electrochim. Acta 2010, 55, 4711.

Jankovic, J., "Levodopa strengths and weaknesses," Neurology 2002, 58, S19.

Jubete, et al., "Electrochemical biosensor development for detection of L-Dopa levels in plasma during Parkinson illness," IEEE Sensors Conf. 2008, 239-241.

Kalachar, et al., "Electrochemical determination of L-dopa in Mucuna pruriens seeds, leaves and commercial Siddha product using gold modified pencil graphite electrode," Electroanal. 2011, 23, 1107.

Kumar, et al., "Levodopa-dyskinesia incidence by age of Parkinson's disease onset," Movement Disord. 2005, 20, 342.

Lee, et al., "The association between cognitive impairment and neuropsychiatric symptoms in patients with Parkinson's disease dementia," J. Int. Psychogeriatr. 2012, 24, 1980.

Lee, et al., "The Role of 3-O-Methyldopa in the Side Effects of L-dopa", Neurochem Res (2008) 33:401-411.

Maricle, et al., "Dose-response relationship of levodopa with mood and anxiety in fluctuating Parkinson's disease," Neurology 1995, 45, 41757.

Metters, et al., "New directions in screen printed electroanalytical sensors: an overview of recent developments," Analyst 2011, 136, 1067.

Moussy, et al., A miniaturized Nafion-based glucose sensor: in vitro and in vivo evaluation in dogs, Int J Artif Organs. 1994;17:88-94.

Muzzi, et al., "Simultaneous determination of serum concentrations of levodopa, dopamine, 3-O-methyldopa and a-methyldopa by HPLC", Biomedicine & Pharmacotherapy 62 (2008) 253-258.

Nagatsu, et al., "A new and highly sensitive voltammetric assay for aromatic I-amino acid decarboxylase activity by high-performance liquid chromatography," Anal. Biochem. 1979, 100, 160.

Nagatsu, et al., "L-dopa therapy for Parkinson's disease: past, present,and future", 2009, Parkinsonism Relat. Disord.15, S3-S8.

Nindl, B., "Insulin-like growth factor-I as a candidate metabolic biomarker: Military televance and future directions for measurement," J. Diabetes Sci. Technol. 2009, 3, 371.

Nindl, et al., "Minimally invasive sampling of transdermal body fluid for the purpose of measuring insulin-like growth factor-I during exercise training," Diabetes Technol. Ther. 2006, 8, 244.

Nyholm, et al., "Duodenal levodopa infusion monotherapy vs oral polypharmacy in advanced Parkinson disease," Neurology 2005, 64, 216.

Obeso, et al., "Levodopa motor complications in Parkinson's disease," Trends Neurosci. 2000, 23, S2.

Pinho, et al., "Electroanalysis of urinary L-dopa using tyrosinase immobilized on gold nanoelectrode ensembles," J. Appl. Electrochem. 2012, 42, 131.

Prabhu, et al., "Amperometric determination of I-dopa by nickel hexacyanoferrate film modified gold nanoparticle graphite composite electrode," Sensor. Actual B-Chem. 2011, 156, 606.

Rascol, et al., "A five-year study of the incidence of dyskinesia in patients with early Parkinson's disease who were treated with ropinirole or levodopa," N. Engl. J. Med. 2000, 342, 1484.

Reddaiah, et al., "Electrochemical investigation of L-dopa and simultaneous resolution in the presence of uric acid and ascorbic acid at a poly (methyl orange) film coated electrode: A voltammetric study," J. Electroanal. Chem. 2012, 682, 164.

Renedo, et al., "Recent developments in the field of screen-printed electrodes and their related applications," Talanta 2007, 73, 202.

Rhemrev-Boom, et al., "A versatile biosensor device for continuous biomedical monitoring," Biosens. Bioelectron. 2001, 16, 839.

* cited by examiner

US 10,364,452 B2

STRIP-BASED ELECTROCHEMICAL SENSORS FOR QUANTITATIVE ANALYSIS OF ANALYTES

CROSS-REFERENCE TO RELATED APPLICATIONS

This patent document is a 35 USC § 371 National Stage application of International Application No. PCT/US2015/033621, entitled "STRIP-BASED ELECTROCHEMICAL SENSORS FOR QUANTITATIVE ANALYSIS OF ANALYTES," which claims the benefits and priority of U.S. Provisional Patent Application No. 62/005,915, entitled "STRIP-BASED ELECTROCHEMICAL SENSORS FOR QUANTITATIVE ANALYSIS OF ANALYTES," filed on May 30, 2014. The entire contents of the aforementioned patent applications are incorporated by reference as part of the disclosure of this application.

TECHNICAL FIELD

This patent document relates to systems, devices, and processes for electrochemical sensing and detection.

BACKGROUND

Sensors based on electrochemical processes can be used to detect a chemical, substance, a biological substance (e.g., an organism) by using a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by optical, electronic or other means. For example, the transduction mechanisms can include physicochemical, electrochemical, optical, piezoelectric, as well as other transduction means.

SUMMARY

Techniques, systems, and devices are disclosed for producing and implementing an electrochemical sensor for quantitative analysis of target analytes in various biological samples. In some aspects, an electrochemical sensor of the disclosed technology includes a multi-electrode contingent on a strip-type substrate including a working electrode providing a layer of single- or multi-walled carbon nanotubes (CNTs) and a polymer-based entrapment layer to contain enzymatic substances to selectively bind to target analytes, which are operable to catalyze a redox reaction producing electrical signals detectable by the electrochemical sensor. In some embodiments, the electrochemical sensor can include a protective layer (e.g., chemical film) over the functionalized working electrode or the entire multi-electrode contingent to provide charge-exclusion or selectively of the electrochemical sensor that allows either positively or negatively charged species and charge neutral species past the protective layer to interact at the electrode, e.g., including the functionalized layer(s) of the working electrode. Exemplary implementations of the disclosed electrochemical sensor can include quantifying the levels of targeted analytes (e.g., such as L-DOPA) in whole blood, plasma, serum, saliva, and/or interstitial fluid samples, e.g., in order to provide the patient and healthcare provider with a quantitative assessment of circulating analyte levels (e.g., L-DOPA levels from oral therapies).

In one aspect, an electrochemical sensor includes a substrate formed of an insulative material; an electrode contingent including a first electrode and a second electrode on the substrate, in which the first electrode includes a coating of carbon nanotubes (CNTs); and an entrapment layer formed on the first electrode to attach an enzymatic substance capable of causing a redox reaction in the presence of a target analyte of a fluid sample which produces a redox-active product, in which the entrapment layer is structured to include a conductive polymer film that is reversibly dopable to conduct charge carriers across the entrapment layer and at the first electrode. Implementations of the electrochemical sensor can include one or more of the following exemplary features. For example, the electrochemical sensor is operable for electrochemical analysis of a fluid sample when the fluid sample is in contact with the electrode contingent, and when the electrochemical sensor is electrically coupled to an electrical circuit to supply an electrical waveform to the electrode contingent to transduce chemical information associated with the target analyte that is present in the fluid sample to an electrical signal. For example, the electrochemical sensor can be formed on a disposable test strip. For example, the conductive polymer film can include poly (thionine), e.g., such that the conductive polymer film is cross-linked to the enzymatic substance using a bovine serum albumin, glutaraldehyde. For example, the enzymatic substance can include tyrosinase, catechol oxidase, polyphenol oxidase, or monophenol monooxygenase, or a combination thereof. For example, in some implementations, the electrochemical sensor can further include a protective layer (e.g., including Nafion) over the entrapment layer on the first electrode, in which the protective layer includes a charge-exclusion material that allows charge neutral species and either positively or negatively charged species to pass through the protective layer.

In one aspect, a method to produce an analyte-selective electrochemical sensor includes providing a signal sensitivity-enhanced electrode on a substrate of an electrochemical sensor including carbon nanotubes (CNTs) on the surface of the electrode; forming an entrapment layer over the signal sensitivity-enhanced electrode by depositing a solution of a polymer material on the surface of the electrode, and applying a fixed potential at the electrode and, subsequently, a continuously-cycled potential with respect to a reference electrode to produce a reversibly dopable conducting polymer film on the electrode; and attaching an enzymatic substance to the entrapment layer by depositing a solution containing the enzymatic substance, an enzyme stabilizing agent, and a cross-linking agent on the conducting polymer film and drying the solution.

In one aspect, a system to detect an analyte in a physiological sample includes a disposable electrochemical test strip sensor and a portable electrochemical analyzer. The electrochemical test strip sensor is structured to include a substrate formed of an insulative material, an electrode contingent including a first electrode having a coating of carbon nanotubes (CNTs) and a second electrode on the substrate, an entrapment layer including a conductive polymer film on the first electrode to attach an enzymatic substance capable of catalyzing a target analyte of a physiological fluid sample, and first and second contact pads on the substrate that are respectively electrically coupled to the first and the second electrodes via electrically conductive conduits. The portable electrochemical analyzer includes a housing including an opening to receive the disposable electrochemical test strip sensor, and an electrical circuit including bonding pads disposed in the opening to electrically couple to the electrochemical test strip sensor via first and the second contact pads when the electrochemical test strip sensor is inserted into the opening, in which the electrical circuit is operable to supply an electrical waveform to the electrochemical test strip sensor to operate an electrochemical analysis technique and to detect electrical signals transduced by the first and second electrodes during the electrochemical analysis technique. The enzymatic substance is provided to cause a redox reaction involving the target analyte when the physiological fluid sample is deposited on the electrodes that produces charge carriers associated with the redox reaction capable of being electrically conducted across the conductive polymer film and detectable at the first electrode by the electrical circuit.

The subject matter described in this patent document can be implemented in specific ways that provide one or more of the following features. For example, the disclosed technology enables a paradigm for the Parkinsonian patient that emulates the glucose test strip for diabetics, facilitating assessment of oral levodopa therapy effectiveness and appropriate dosing adjustment. An exemplary method to produce an exemplary embodiment of the disclosed electrochemical sensor devices includes the following. A three-electrode electrochemical sensor is screen printed on a substrate. The sensor can include an Ag/AgCl conductive underlayer and reference electrode, a graphitic carbon working electrode and an electrically insulative layer. On the surface of the working electrode is a dispersed solution of single- or multi-walled carbon nanotubes (CNTs). The working electrode is subsequently desiccated, after which a solution of thionine is deposited on the working electrode. A fixed potential is then applied at the working electrode. Subsequently, the applied potential is continuously cycled over a pre-determined range for a set number of potential cycles (e.g., cyclic voltammetry). This can result in the generation of a poly(thionine) film on the working electrode. Optionally, the sensor is subsequently conditioned in a phosphate buffer solution by again cycling the potential at the working electrode for a given number of cycles. Next, a phosphate buffer solution containing bovine serum albumin (e.g., for enzyme stabilization), glutaraldehyde (e.g., for enzyme cross-linking/immobilization), and the enzyme tyrosinase, catechol oxidase, polyphenol oxidase, or monophenol monooxygenase (e.g., leveraged to biocatalytically oxidize L-DOPA) is dispensed on the working electrode and allowed to cross-link and desiccate at room temperature. A Nafion film is finally cast on the surface of the working electrode, which is allowed to dry at room temperature. The exemplary L-DOPA-selective electrochemical biosensor strip is thus ready for use or storage for future use.

In operation, for example, the exemplary three-electrode biosensor strip device can be utilized for quantitative analysis of a target analyte (e.g., L-DOPA) by placing the device in contact with a physiological fluid sample, e.g., such as blood, plasma, serum, interstitial fluid, or saliva. A chemical reaction ensues whereby the enzyme biocatalytically oxidizes L-DOPA present in the sample to dopaquinone. In the presence of dopaquinone, the poly(thionine) film on the working electrode is oxidized, which concomitantly serves to reduce dopaquinone back to L-DOPA. The strip is subsequently inserted into a handheld meter containing an electrochemical analyzer (e.g., potentiostat). A small electrical potential is applied at the working electrode (e.g., amperometry) with respect to the reference electrode and a current subsequently flows between the working and counter electrodes. The oxidized poly(thionine) present on the working electrode is converted to a reduced form of poly(thionine). The magnitude of this electron flow between the working electrode and counter electrode or vice versa is regulated by the chemical reaction and can be measured using the potentiostat. The magnitude of the current measured with respect to time will be proportional to the concentration of the analyte, in this exemplary case L-DOPA, in the physiological fluid sample.

DETAILED DESCRIPTION

Figure 1A:
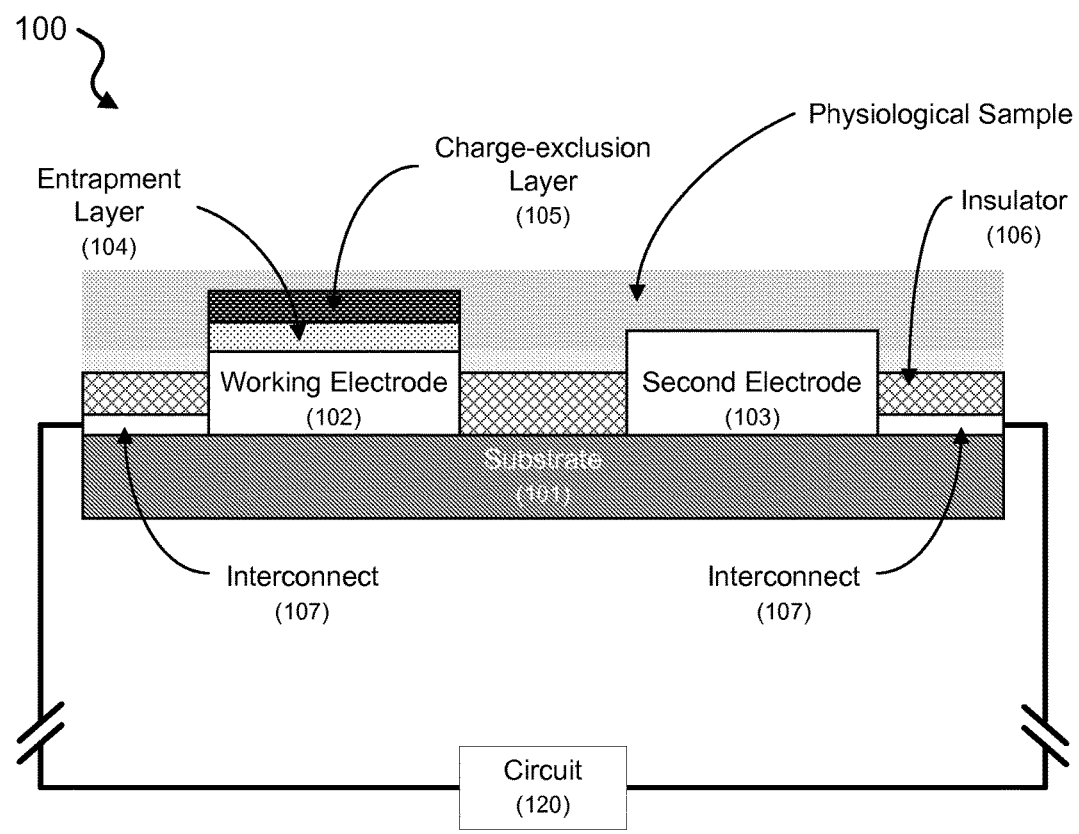
FIGS. 1A and 1B show block diagrams of exemplary electrochemical sensors of the disclosed technology.

Oral L-DOPA (L-3,4-dihydroxyphenylalanine) or levodopa supplements are widely used to increase dopamine concentrations in the treatment of Parkinson's disease and dopamine-responsive dystonia. The administration of levodopa therapies is highly individualized and must be dosed in accordance with the control of symptoms. Hence there is no "standard dose" of levodopa. Moreover, to maintain the same therapeutic effect, often the levels of L-DOPA must be gradually increased. The Parkinsonian thus returns to the healthcare provider on a frequent basis for evaluation via visual assessment, patient testimony and, in rare cases, a blood sample for L-DOPA quantification, a costly proposition that typically takes 2-3 weeks. A cost-effective, easy-to-perform technique is needed to provide individualized feedback on a proper levodopa dosing regimen in a decentralized and rapid fashion.

Techniques, systems, and devices are disclosed for producing and implementing an electrochemical sensor for quantitative analysis of target analytes in various biological samples. In some aspects, an electrochemical sensor of the disclosed technology includes a multi-electrode contingent on a strip-type substrate including a working electrode providing a layer of single- or multi-walled carbon nanotubes (CNTs) and a polymer-based entrapment layer to contain enzymatic substances to selectively bind to target analytes, which are operable to catalyze a redox reaction producing electrical signals detectable by the electrochemical sensor. In some embodiments, the electrochemical sensor can include a protective layer (e.g., chemical film) over the functionalized working electrode or the entire multi-electrode contingent to provide charge-exclusion or selectively of the electrochemical sensor that allows either positively or negatively charged species and charge neutral species past the protective layer to interact at the electrode, e.g., including the functionalized layer(s) of the working electrode. The disclosed electrochemical sensing devices, systems, and methods can be used for quantifying levels of targeted analytes (e.g., such as L-DOPA) in whole blood, plasma, serum, saliva, and/or interstitial fluid samples, e.g., in order to provide the patient and healthcare provider with a quantitative assessment of circulating analyte levels.

While the disclosed embodiments are described herein primarily based on L-DOPA detection and quantitative analysis to facilitate understanding of the underlying concepts, it is understood that the disclosed embodiments can also include monitoring of other analytes in physiological fluid samples, e.g., including dopamine, norepinephrine, epinephrine, among other neurotransmitters. For example, the disclosed electrochemical sensor technology can be used to detect and quantitatively assess glucose, lactate, uric acid, ascorbic acid, ketone bodies, amino acids, and other metabolites.

L-DOPA (L-3,4-dihydroxyphenylalanine) is a chemical that is naturally synthesized in the nervous system from the amino acid L-tyrosine and serves as the precursor to the neurotransmitters dopamine, norepinephrine, epinephrine, collectively known as catecholamines. L-DOPA crosses the protective blood-brain barrier, whereas the catecholamine neurotransmitters themselves cannot. Since the 1960s, it has been used as a drug for the treatment of Parkinson's disease, which is caused by deficiency of the neurotransmitter dopamine and remains the best therapeutic agent for the condition. L-DOPA is a precursor of dopamine, and since it is able to cross the blood-brain barrier while dopamine itself cannot, it is used to increase dopamine levels. Thus, oral L-DOPA supplements (levodopa) are widely used to increase dopamine concentrations in the treatment of Parkinson's disease and dopamine-responsive dystonia. On the other hand, long term use of L-DOPA can lead to dyskinesias and other side effects. As a consequence, the control of its levels in serum or blood during therapy is vital.

The administration of levodopa therapies is highly individualized and must be dosed in accordance with the control of symptoms, which are highly variable among individuals. Hence there is no "standard dose" of levodopa. Moreover, during the course of treatment, it is often the case that, to maintain the same therapeutic effect, the levels of L-DOPA must be gradually increased as treatment ensues whereas the threshold for side-effects such as dyskinesia, deterioration of fine motor function, and freezing during movement reduces, resulting in a narrow window of therapeutic effectiveness for a given dose. The Parkinsonian must return to the healthcare provider on a frequent basis to evaluate the therapy's effectiveness and adjust the dosing for proper control of the disease. This evaluation is performed via a visual assessment of fine motor control and patient testimony on frequency and severity of tremors and, in very rare cases, a blood sample is sent to a centralized laboratory for L-DOPA quantification, a costly proposition that typically takes 2-3 weeks. Accordingly, a cost-effective, easy-to-perform technique is needed to provide individualized feedback on a proper levodopa dosing regimen in a decentralized and rapid fashion.

The disclosed electrochemical sensing technology includes methods and low-cost printed electrochemical sensor devices capable of quantifying the levels of L-DOPA, e.g., in whole blood, plasma, serum, interstitial fluid, or saliva samples, in order to provide the patient and healthcare provider with a quantitative assessment of circulating L-DOPA levels from oral therapies. In this manner, this paradigm emulates a glucose test strip for individuals afflicted with diabetes. This endows the Parkinsonian patient (or their caregiver) the ability to accurately assess effectiveness of their oral levodopa therapy and adjust dosing contingently. It can also provide the healthcare provider with a capability to review trends in circulating L-DOPA and make a more informed decision regarding proper levodopa dosing on an individual basis in order to maximize effectiveness while mitigating the likelihood of side-effects.

The disclosed technology represents the first capability to quantify L-DOPA levels in blood, plasma, serum, saliva, or interstitial fluid samples using electrochemical methods, as demonstrated in exemplary implementations described below. The disclosed devices and methods are extremely low in cost, easy-to-use, and easily deployable (e.g., as a handheld meter and electrochemical strip contingent).

Existing, conventional methods for the quantification of L-DOPA in blood samples leverage high-performance liquid chromatography (HPLC) whereby the constituents of a blood sample are separated in a column containing adsorbent material owing to differences in flow rates. Due to the cost of executing such a test, it is rarely performed and hence the healthcare provider must make qualitative assessments (e.g., frequency and intensity of tremors, patient testimony) of the effectiveness of oral levodopa therapies.

Exemplary electrochemical sensor devices and methods to produce the disclosed electrochemical sensor devices can include the following. FIG. 1A shows a block diagram of the exemplary electrochemical sensor 100 of the disclosed technology. The electrochemical sensor 100 includes a substrate 101, which includes an electrically insulative material, and which can be configured as a test strip for an electrochemical analyzer device. The electrochemical sensor 100 includes a multi-electrode contingent, e.g., which can include a two electrode contingent or a three electrode contingent, or arrays of such multi-electrode contingents, on the substrate 101. In the example shown in FIG. 1A, the electrochemical sensor 100 includes a working electrode 102 and a second electrode 103 separately disposed on the substrate 101. The electrochemical sensor 100 includes electrical interconnects 107 (e.g., including an electrically conductive material) to conduct electrical signals from the electrodes of the multi-electrode contingent to bonding or contact pads (not shown) formed on the substrate 101, e.g., to electrically interface with a circuit 120 to provide electrical signals for electrochemical analysis of a physiological sample on the electrode contingent and analyze the detected electrical signals by the electrode contingent. In some embodiments, for example, the electrochemical sensor 100 can include an insulator layer or structure 106, e.g., which can provide further structural support for the electrochemical sensor 100 and protect the electrical signal integrity of conducted electrical signals through the electrodes and the interconnects or conduits 107.

For example, the electrode configuration of the disclosed electrochemical sensor devices can be designed based on the type of target analyte to be sensed and the type of detection methodology, e.g., amperometry, chronoamperometry, voltammetry, cyclic voltammetry, potentiometry, chronopotentiometry, and/or electrochemical impedance spectroscopy, or other electrochemical analysis technique, to be employed. In some examples, the electrochemical sensor 100 can be configured to detect charged analytes, e.g., using potentiometry. In some embodiments, for example, the electrochemical sensor 100 can include a third electrode on the substrate such that the working electrode 102 is positioned between the third electrode and second electrode 103; in which the second electrode 103 and the third electrode can serve as a counter electrode 113 and a reference electrode 114 in an electrochemical analysis technique, respectively, as depicted in the block diagram of example electrochemical sensor 110 shown in FIG. 1B. In some embodiments, for example, the electrochemical sensor 100 can include an array of electrode contingents, e.g., such as an array of working electrodes and reference electrodes, and/or counter electrodes.

Figure 1B:
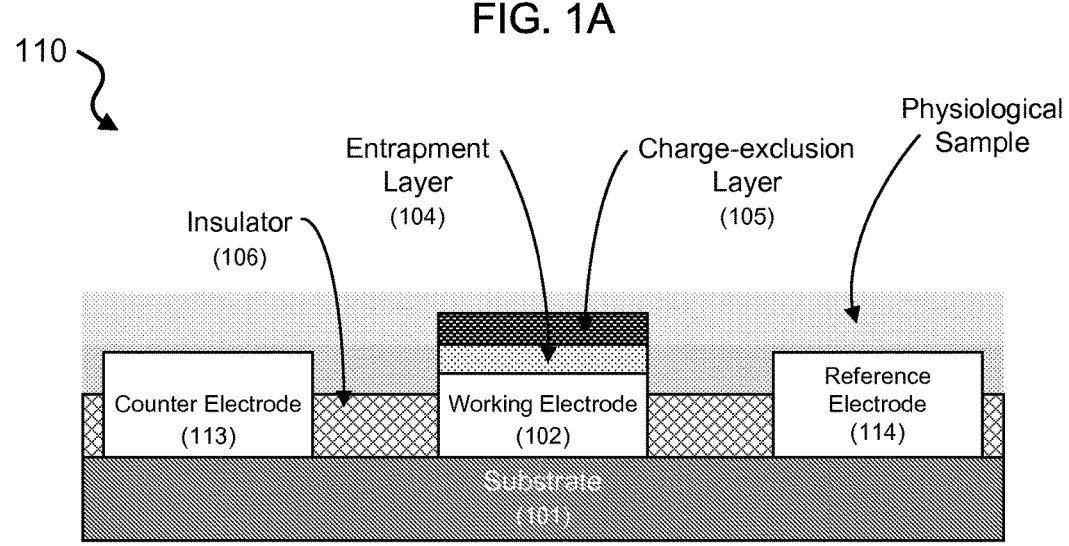

Referring to FIGS. 1A and 1B, in some exemplary implementations, the working electrode 102 includes a layer designed to improve signal sensitivity, which can include carbon nanotubes (CNTs) attached to the electrically conductive material of the working electrode 102. In some implementations, for example, the working electrode 102 includes an entrapment layer 104 structured to include a conductive polymer coating (e.g., a poly(thionine) film) that (1) entraps an bio-recognition or biocatalytic substance, e.g., such as an antibody or enzyme, capable of binding to a target chemical agent to contain sustain a redox reaction at the working electrode 102 to produce a detectable electrical signal that can be detected using the electrode contingent, e.g., amperometry, voltammetry, and/or potentiometry, impedimetry, conductimetry, coulometry, and/or polarography; and (2) conducts the electrical charge produced during the redox reaction involving the redox-active products by which the conductive polymer coating undergoes a change in the charge state of the conductive polymer coating. For example, the entrapped enzymatic substance that can facilitate the redox reaction with a target analyte in the physiological fluid sample that produces one or more products that are redox-active and able to be sensed by the working electrode 102 via the conductive polymer coating of the entrapment layer 104. The working electrode 102 can also include a charge-exclusion layer 105 (e.g., such as Nafion) to selectively allow chemical species of a certain charge (i.e., positively-charged species or negatively-charged species) and charge neutral species (e.g., such as L-DOPA) through the layer 105 to the entrapment layer 104.

The entrapment layer 104 is structured to include a redox-active conductive polymer material that can be selectively doped during a redox reaction where the charge state can change based on the addition or removal of charge carriers produced via the redox reaction. For example, the conductive polymer material can include poly(thionine) as the redox-active conducting polymer that can provide a structural matrix to entrap the enzymatic substance and become selectively doped in the presence of a redox-active product (e.g., such as dopaquinone) arising from a biocatalytic reaction facilitated by the enzyme substance (e.g., tyrosinase). For example, the selective doping of the redox-active conducting polymer includes the addition or removal of charge carriers, e.g., electrons or holes, in the molecular matrix of the redox-active conducting polymer. On one hand, for example, the redox-active conducting polymer poly(thionine) can be oxidized/p-doped in the presence of dopaquinone, which serves to remove electrons from the polymer molecular matrix, thereby becoming a polymer structure analogous to a p-type semiconductor material; whereas on the other hand, for example, the poly(thionine) can be reduced/n-doped due to an electrical current applied at the working electrode based on reduction to add electrons to become a polymer structure analogous to a n-type semiconductor material.

In operations, for example, the electrochemical sensor 100 or 110 can be electrically interfaced with the circuit 120 for electrochemical analysis of the target analyte (e.g., L-DOPA) when the physiological fluid sample is present on the electrochemical contingent of the sensor 100. For example, the circuit 120 can apply excitation waveforms and/or transduce the electrical signals generated by the electrochemical electrodes of the electrochemical sensor 100 upon excitation. In some examples, the circuit 120 can be part of a portable electrochemical analyzer device that includes a signal conditioning unit, data processing unit, and/or communication unit to transmit the acquired and/or processed data to another external device, e.g., such as a desktop or laptop computer, a communication network of computers, and/or a mobile computing device, e.g., such as a smartphone, tablet, smartglasses, smartwatch, or other wearable computing and/or communications device. The circuit 120 can be structured to include, but not limited to, a potentiostat (e.g., to realize amperometric and voltammetric measurements) or a galvanostat (e.g., to realize potentiometric measurements).

Figure 2A:
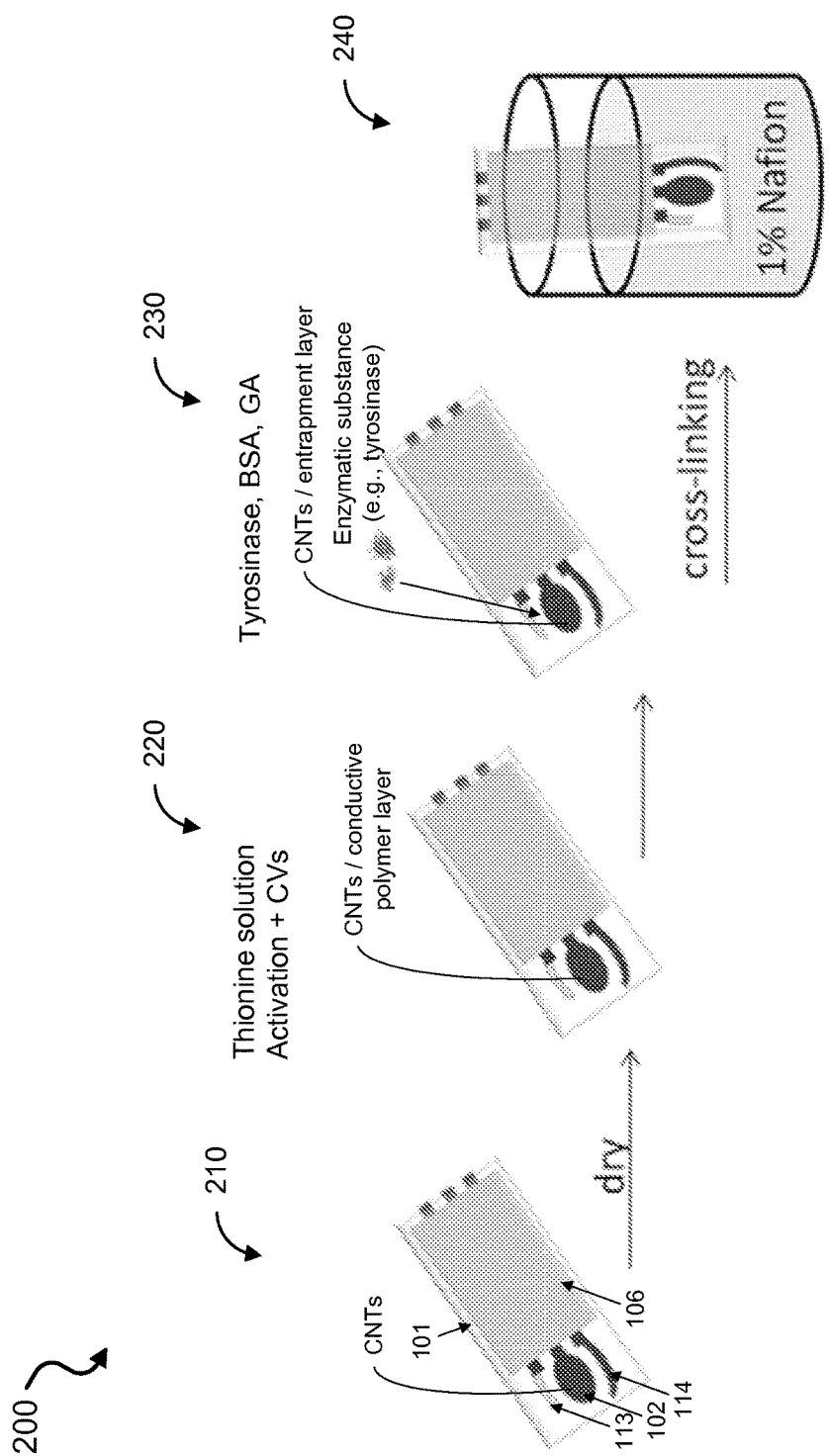
FIG. 2A shows an illustrative diagram of an exemplary method to produce an electrochemical biosensor of the disclosed technology.

The exemplary constituents of the electrochemical sensor 100 can include an Ag/AgCl conductive underlayer and reference electrode, a graphitic carbon working electrode (e.g., which can be configured to contain dispersed single- or multi-walled carbon nanotubes), and an electrically insulative layer (e.g., which can be configured of a plastic, polymer, or epoxy) to define the active geometry of the device, as shown in FIG. 2A. FIG. 2A shows an illustrative diagram of an exemplary method 200 to produce the exemplary electrochemical sensor 100. The method 200 includes a process 210 to provide a signal sensitivity enhanced electrode to serve as the working electrode 102 of the electrochemical sensor 100 or 110. In some implementations of the process 210, for example, the process 210 can include depositing on the surface of a formed working electrode 102 a dispersed solution of single- or multi-walled carbon nanotubes (CNTs), or otherwise containing the CNT solution thereon. In such implementations of the process 210, for example, the working electrode 102 (e.g., containing the dispersed solution) is subsequently dried (e.g., desiccated). In other implementations of the process 210, for example, the process 210 can include forming a carbon-based working electrode using a conductive ink material that contains CNTs within the ink. In such implementations, for example, the working electrode 102 with the signal enhancing capability can be formed in a single-step using a screen-printing technique to produce a screen-printed electrode (SPE) having the CNTs present in and/or on the surface of the working electrode. The method 200 includes a process 220 to produce the conductive polymer layer of the entrapment layer 104 by, e.g., depositing a solution of thionine (e.g., in phosphate buffer) on the working electrode 102, or otherwise containing the thionine solution thereon. For example, in implementations of the process 220, a fixed potential can then be applied at the working electrode (with respect to the reference electrode) for a short period of time. Subsequently, the applied potential is continuously cycled over a predetermined range (in a technique known as cyclic voltammetry) for a set number of potential cycles. This can result in the generation of a conducting poly(thionine) polymer film on the working electrode. Optionally, the sensor 100 can be subsequently conditioned in a phosphate buffer solution by again cycling the potential at the working electrode for a given number of cycles. The method 200 includes a process 230 to attach the enzymatic substance in the entrapment layer 104, e.g., by dispensing a phosphate buffer solution containing bovine serum albumin (for enzyme stabilization), glutaraldehyde (for enzyme cross-linking/immobilization), and the enzyme tyrosinase, catechol oxidase, polyphenol oxidase, or monophenol monooxygenase (leveraged to biocatalytically oxidize L-DOPA) on the working electrode 102, and subsequently allowing to cross-link and dry (e.g., desiccate at room temperature). In some implementations of the method 200, for example, the method 200 includes a process 240 to produce the protective layer 105, e.g., by forming a Nafion film on the surface of either the working electrode or the entire electrode contingent (e.g., two or three electrode contingent), e.g., by casting a Nafion solution (e.g., 1% Nafion solution) on the sensor 100 surface and allowing to dry (e.g., at room temperature, e.g., for 15 minutes), and then repeating multiple times (e.g., repeating two more times). The exemplary L-DOPA-selective electrochemical biosensor strip is thus ready for use or storage for future use.

In some exemplary operations of the exemplary three-electrode biosensor strip device, the user can employ a lancet or other skin-piercing device to access a small blood sample. Among other locations, this blood sample can be taken from the fingertip, hand, arm, deltoid, abdomen, or ear lobe. The exemplary electrochemical biosensor strip above can then be placed in contact with the blood to draw the sample to the electrode contingent via capillary action. A chemical reaction ensues whereby the enzyme (e.g., tyrosinase, catechol oxidase, polyphenol oxidase, or monophenol monooxygenase) biocatalytically oxidizes L-DOPA to dopaquinone while simultaneously reducing free oxygen to form water. In the presence of dopaquinone, the poly(thionine) film on the working electrode is oxidized, which concomitantly serves to reduce dopaquinone back to L-DOPA.

Figure 2B:
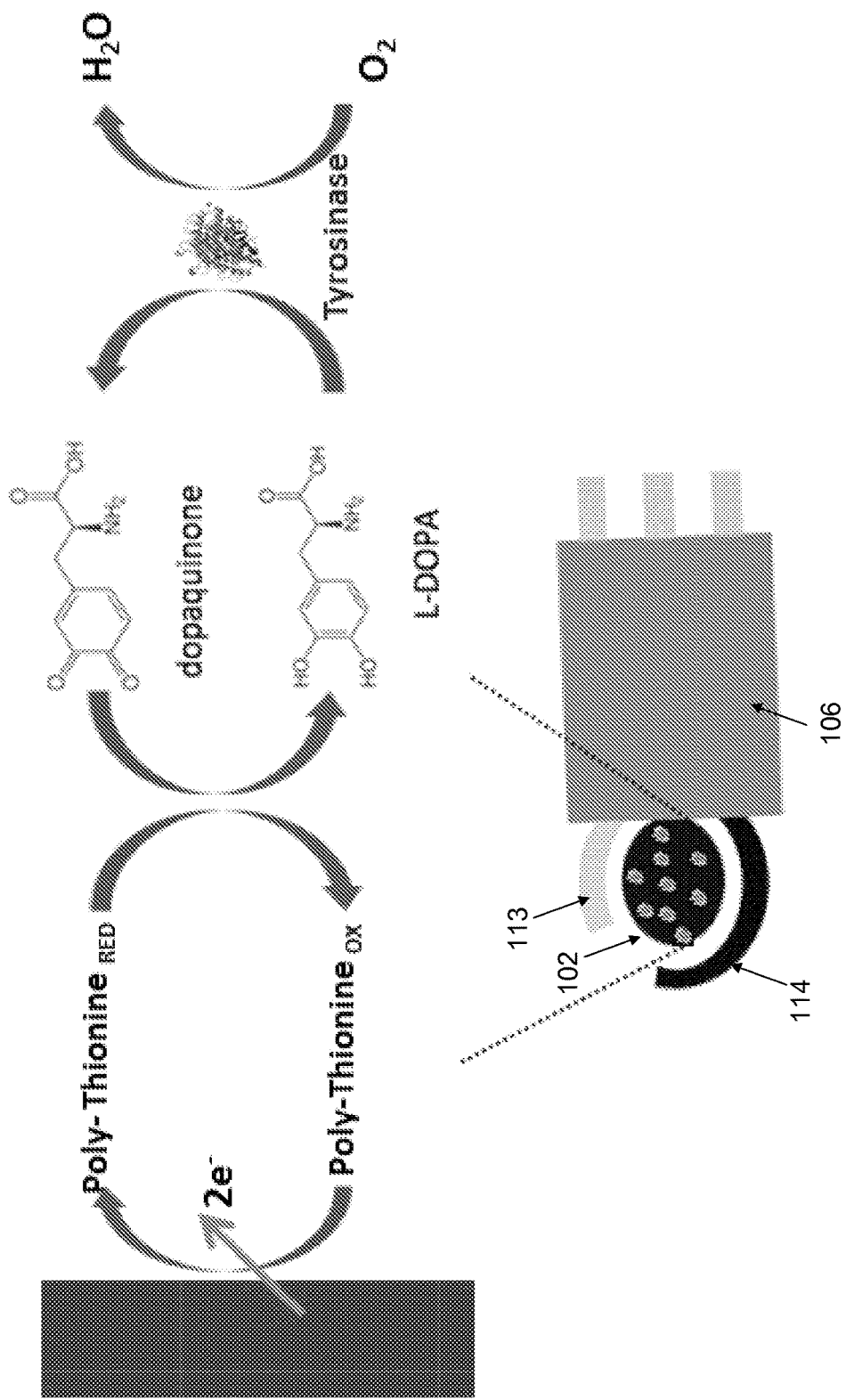
FIG. 2B shows an illustrative diagram of an exemplary enzymatic and electrochemical reaction in an exemplary implementation of the exemplary electrochemical biosensor shown in FIG. 2A.

FIG. 2B shows an illustrative diagram of an exemplary enzymatic and electrochemical reaction in an exemplary implementation of the electrochemical biosensor 100 shown in FIG. 2A. In the example shown in FIG. 2B, the entrapment layer 104 includes poly(thionine) that entraps the enzyme tyrosinase for the detection and quantitative analysis of the L-DOPA analyte in a physiological fluid.

The strip can be subsequently inserted into a handheld meter containing an electrochemical analyzer (e.g., potentiostat). A small electrical potential is applied at the working electrode with respect to the reference electrode (e.g., to obtain amperometric electrochemical measurements), in which a current subsequently flows between the working and the counter electrode. In a two-electron transfer process, the oxidized poly(thionine) present on the electrode (resulting from the chemical oxidation of poly(thionine) imparted by the presence of dopaquinone) is converted to a reduced form of poly(thionine). The magnitude of this electron flow (e.g., electrical current between the working electrode and counter electrode, or vice versa) is regulated by the chemical reaction (specifically the amount of reactant, L-DOPA) and can be measured using the potentiostat. By merit of electrochemical principles, e.g., namely the Cottrell equation, the magnitude of the current measured with respect to time will be proportional to the concentration of the analyte (in this example case, L-DOPA) in the physiological fluid sample. The value measured for the electrical current can indicate a quantitative level (e.g., concentration level) of the analyte in the sample, e.g., such as by being inserted into a calibration equation or compared with a calibration table in order to determine the actual L-DOPA concentration corresponding to this reading.

The disclosed electrochemical sensor methods and devices have numerous applications in the diagnostics and therapeutics domain. In one example, the present technology can be used in the assessment of proper dosing regimens for oral levodopa therapies required for the management of Parkinson's disease and dopamine-responsive dystonia. Accordingly, the disclosed technology can be leveraged to identify proper dosing levels of medications while minimizing the risk of over-dosing, which frequently results in harmful side-effects. In this manner, any individual that takes oral levodopa supplements could benefit from the present technology as it does away with the need for frequent visits to the clinic for qualitative neurological evaluation, thus alleviating the burden on both the patient and the healthcare provider. It also enables the individual to take proactive measures to properly dose levodopa (much like dosing insulin injections via blood glucose readings) to facilitate a less-dependent lifestyle.

In some exemplary embodiments of the disclosed electrochemical sensor technology, a disposable electrochemical biosensor test strip for the determination of L-DOPA in biological fluids includes an electrically insulative substrate and an electrode contingent including a carbon nanotube-modified screen printed working electrode covered with an electropolymerized poly(thionine) film and an outer cross-linked layer containing tyrosinase, catechol oxidase, polyphenol oxidase, or monophenol monooxygenase, and a counter/reference electrode(s). In some implementations, for example, the disposable electrochemical biosensor test strip further includes coverage of the sensor (e.g., functionalized working electrode, or all of the electrodes of the electrode contingent) with a protective charge-exclusion layer (e.g., Nafion layer) to allow only selected species in the physiological medium beyond the layer, thereby enabling the disposable electrochemical biosensor test strip's use directly in unprocessed physiological fluids, and obviating the need for sample pretreatment. In exemplary implementations of the exemplary disposable electrochemical biosensor test strip for L-DOPA detection and analysis, for example, the sensor exhibited linear behavior in the 0.8-22 $\mu M$ concentration range, as described later in this patent document.

An important step in the fabrication of biosensors is the effective attachment of the enzyme onto the electrode surface. For example, a tyrosinase biosensor can be prepared based on the immobilization of the enzyme in an inner cross-linked layer containing the enzyme itself with an electropolymerised film of poly(thionine) on top. For example, the poly(thionine) can enhance the stability of the sensor and is and is a redox mediator.

The present technology includes a disposable electrochemical biosensor for targeted analyte detection and quantitative analysis (e.g., including L-DOPA determination) in physiological fluid samples. The exemplary disposable electrochemical sensors of the present technology include the use of functionalized electrodes, e.g., such as an outer cross-linked layer containing tyrosinase on the top of a carbon nanotubes (CNTs) modified screen printed electrode/poly(thionine) film. This exemplary reagent layer not only enhances signal and stability but also facilitates a low detection limit of L-DOPA in clinical samples.

Exemplary Implementations

Exemplary implementations of the exemplary disposable electrochemical biosensor for L-DOPA detection, which included the following methods and materials for fabrication and characterization.

Exemplary materials included tyrosinase (e.g., from mushroom, EC 1.14.18.1) thionine acetate, bovine serum albumin, 3,4-dihydroxy-L-phenylalanine (L-DOPA), glutaraldehyde, Nafion, sodium phosphate monobasic, sodium phosphate dibasic and sodium chloride, which were obtained and were used without any further purification. Carbon nanotubes (e.g., C grade) were used. Ultrapure deionized water (18.2 MΩ-cm) was used in the exemplary implementations. The exemplary implementations were performed either with, for example, phosphate buffer (PBS) prepared using disodium hydrogen phosphate and sodium dihydrogen phosphate (0.1 M, pH 7.2) in ultrapure deionized water with 0.1 M sodium chloride added or undiluted human serum Exemplary instrumentation included CH Instruments (Austin, Tex.) model 1232A electrochemical analyzer, which was employed for the exemplary electrochemical implementations. The exemplary measurements were conducted using a three-electrode configuration including the screen-printed electrochemical sensor (SPE). The working electrode (3 mm diameter) was carbon, printed with a carbon counter electrode and an Ag/AgCl reference electrode. The exemplary electrochemical measurements were performed with a 100 µL sample, which was dispensed onto the electrode surface. The exemplary electrochemical measurements were performed at room temperature (22±2° C.).

Exemplary fabrication methods to produce the exemplary electrochemical biosensor included the following. A film of carbon nanotubes (CNTs) was cast on the surface of the working electrodes by dispensing 2 µL of CNTs solution (e.g., 2.3 mg/mL) and allowing the surface to dry overnight. The electrodes were subsequently covered by an electrochemically deposited poly(thionine) film. Electropolymerization was performed. At first, the electrode was covered dispensing 60 µL of a 0.25 mM thionine solution (in PBS), and then applying constant potential at +1.2 V for 2 min (e.g., thionine activation). Then, the poly(thionine) film was grown in the same solution by cycling the potential between −0.6 V and +0.1 V at 100 m Vs$^{-1}$ for 20 cycles. After the polymerization, the sensor was conditioned in PBS cycling the potential between −0.5 V and +0.1 V vs Ag/AgCl at 0.1 Vs$^{-1}$ for 40 cycles.

The enzymatic solution was prepared by mixing 1.4 mg of tyrosinase, 10 µL BSA (1 mg/mL final concentration), 90 µL PBS and 1 µL 2.5% glutaraldehyde. 2.5 µL of this mixture was then casted onto the working electrode surface and allowed to cross-link (overnight) at room temperature. The resulting enzyme activity was of 58.8 units on the surface, assuming no leakage.

For use in serum samples, for example, the whole SPE-biosensor was covered with a Nafion solution. The exemplary procedure included: immersing the whole sensor in a 1% Nafion solution for 30 s and allowing the surface to dry at room temperature for 15 min. The procedure was repeated three times. The protective layer was selected owing to its biocompatible nature that is compatible for use in physiological fluids. The exemplary results were obtained with Nafion-coated working electrodes. When not in use, the biosensors were stored at 4° C.

The exemplary implementations included chronoamperometric characterizations. For example, determination of L-DOPA was performed by measuring the intensity of current corresponding to the electrochemical reduction of the enzymatically generated dopaquinone and the subsequent poly(thionine) reduction. This was accomplished by dispensing a known volume of the sample onto the sensor and applying a constant potential of −0.31 V. Chronoamperograms for different L-DOPA concentration were recorded and the current was sampled after 2 minutes.

The electrochemical behavior of L-DOPA was investigated via cyclic voltammetry (CV) at the unmodified screen printed electrode (SPE), at the SPE modified with CNTs, and at an example electrochemical biosensor (e.g., CNTs/polythionine). This was conducted to determine the most favorable potential for the reduction reaction and consequently the conditions for the amperometric measurements.

Figure 3:
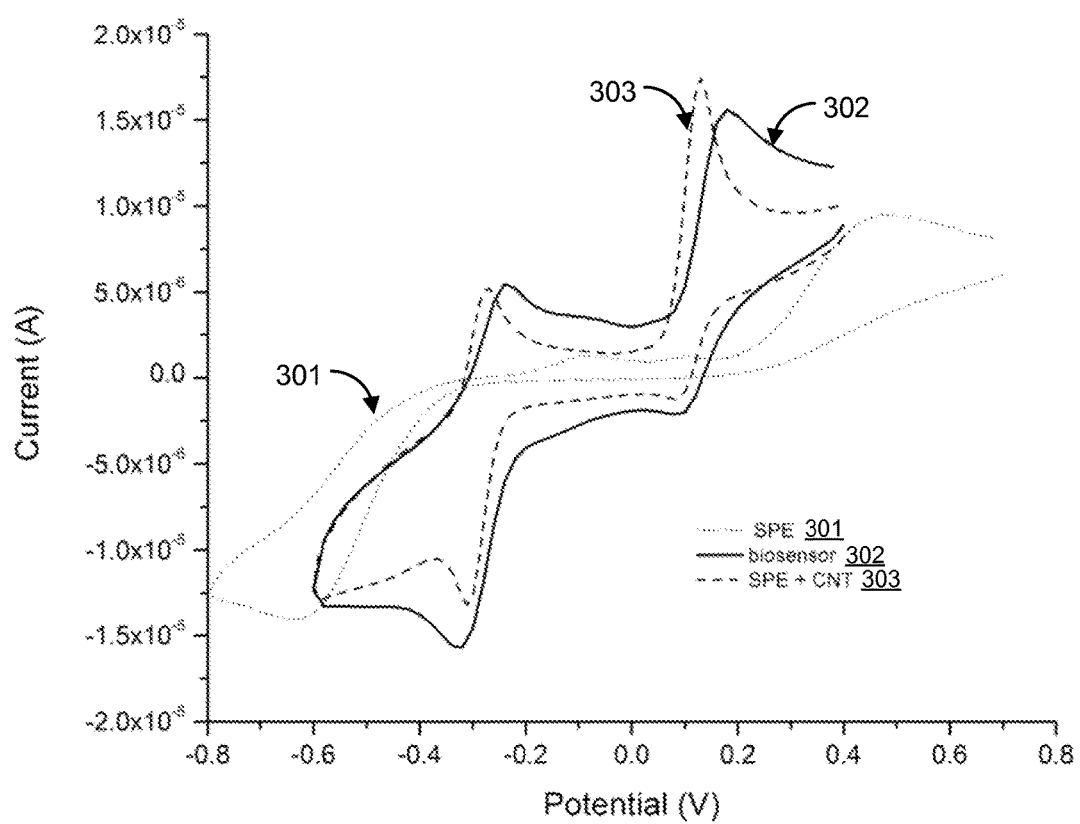
FIG. 3 shows a data plot of cyclic voltammograms using control electrodes and functionalized electrodes of an exemplary electrochemical sensor device of the disclosed technology in a 1 mM L-DOPA solution.

FIG. 3 shows a data plot of cyclic voltammograms using control electrodes and functionalized electrodes of an exemplary electrochemical sensor device of the disclosed technology in a 1 mM L-DOPA solution, e.g., recorded at a bare SPE electrode 301, a CNT/polythionine sensor electrode 302, and at a CNTs-modified SPE 303, in which the supporting electrolyte was pH 7.2 PBS with 0.1M NaCl, and the scan rate was: 0.05 Vs$^{-1}$. As shown in the data plot of FIG. 3, the L-DOPA response exhibited well-defined and sharp peaks at the CNT-modified electrode 303; whereas at the unmodified SPE 301, only a weak response was detected. This data demonstrates the active role of the exemplary CNTs in increasing the sensor sensitivity and reaction reversibility.

The exemplary data shown in FIG. 3 depicts the redox reaction involving the oxidation of L-DOPA to its orthobenzoquinone derivative and the following reduction back to L-DOPA. For example, at the CNT/polythionine sensor 302, L-DOPA was oxidized at 0.176 V vs Ag/AgCl and the dopaquinone was reduced at 0.086 V vs Ag/AgCl and thereafter at −0.326 V. There is also a peak at −0.236 V vs Ag/AgCl, assigned to cyclodopa. At the only CNT-modified electrode 303 the corresponding potentials are slightly changed, L-DOPA was oxidized at 0.130 V vs Ag/AgCl while the reduction peaks were at 0.084 V and −0.310 V vs Ag/AgCl, respectively; a clear enhancement in the reduction signal due to the polythionine was observed in the cyclic voltammograms. The cyclodopa peak transitioned to −0.273V vs Ag/AgCl.

Figure 4:
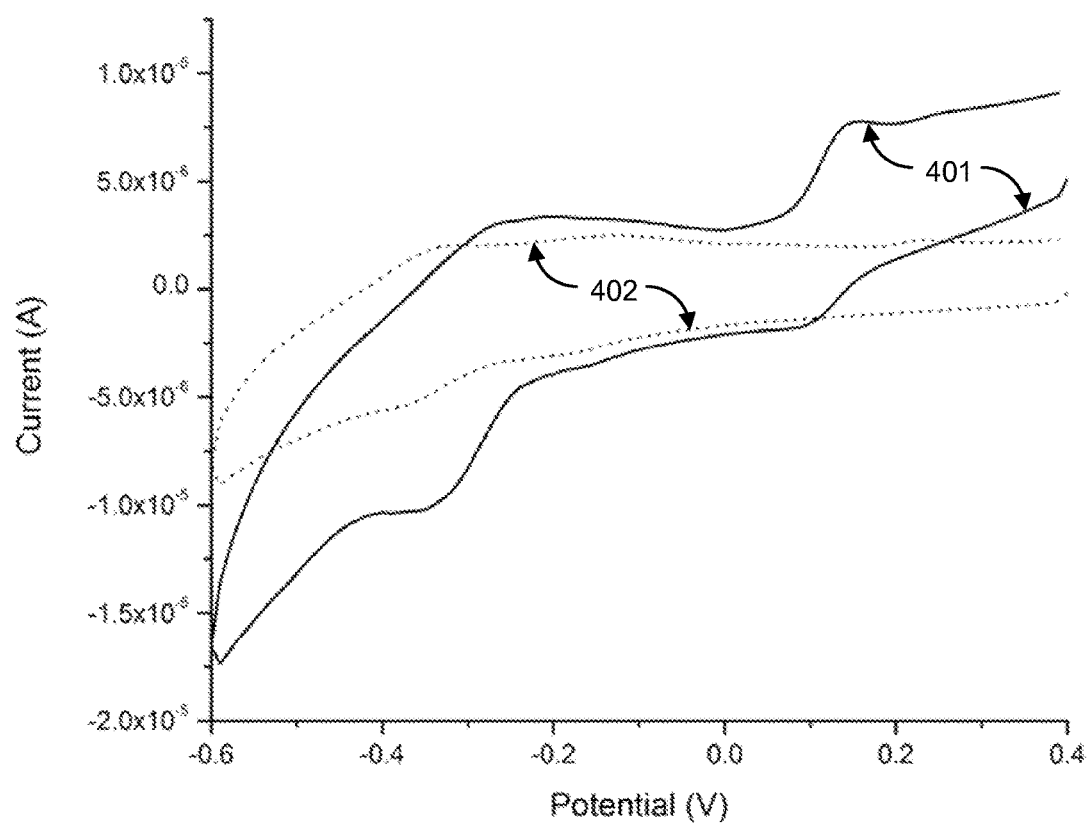
FIG. 4 shows a data plot of cyclic voltammograms recorded using control electrodes and functionalized electrodes of an exemplary electrochemical sensor device of the disclosed technology in a 1 mM L-DOPA spiked serum sample and unspiked serum sample.

FIG. 4 shows a data plot of cyclic voltammograms recorded using control electrodes and functionalized electrodes of an exemplary electrochemical sensor device of the disclosed technology in a 1 mM L-DOPA spiked serum sample 401 (continuous line) and an unspiked serum sample 402 (dotted line), e.g., in which the scan rate was: 0.05 Vs$^{-1}$. As shown in FIG. 4, when using a CNTs/polythionine sensor in a serum sample spiked with L-DOPA, the oxidation peak at the Nafion-covered sensor shifts from 0.176 to 0.150 V vs Ag/AgCl while the corresponding reduction potential is practically unchanged. The cyclodopa peak is shifted from −0.236 V vs Ag/AgCl in the supporting electrolyte to −0.25 V vs Ag/AgCl in the serum sample. The most noticeable difference is the diminished peak height and their broader shape.

The exemplary implementations include amperometric detection. The immobilized tyrosinase catalyzes the oxidation of L-DOPA to orthoquinone, and the reduction of the latter should give rise to a current at the reduction potential determined with the cyclic voltammetric experiments. For example, as a consequence, the recorded current should be directly proportional to the L-DOPA concentration. As shown earlier, the reduction potential is around −0.31 V vs Ag/AgCl. Based on this information, the exemplary implementations were made evaluating the optimal reduction potential by adjusting the value in the −0.26 to −0.46 V vs Ag/AgCl range. At −0.26 V vs Ag/AgCl, no changes in the current recorded at the sensor were observed following increasing additions of L-DOPA. Starting from −0.31 V vs Ag/AgCl, a linear variation of the current was observed with increasing analyte concentration. The best linear relationship was obtained applying −0.31 V vs Ag/AgCl as the reduction potential, so this value was chosen for all the further implementations described herein.

Data obtained analyzing L-DOPA standard solutions in PBS, allowed for the estimation of the functional relationship (current vs concentration), which enabled the determination of a linear response in the 0.4-16 µM concentration range.

Figure 5:
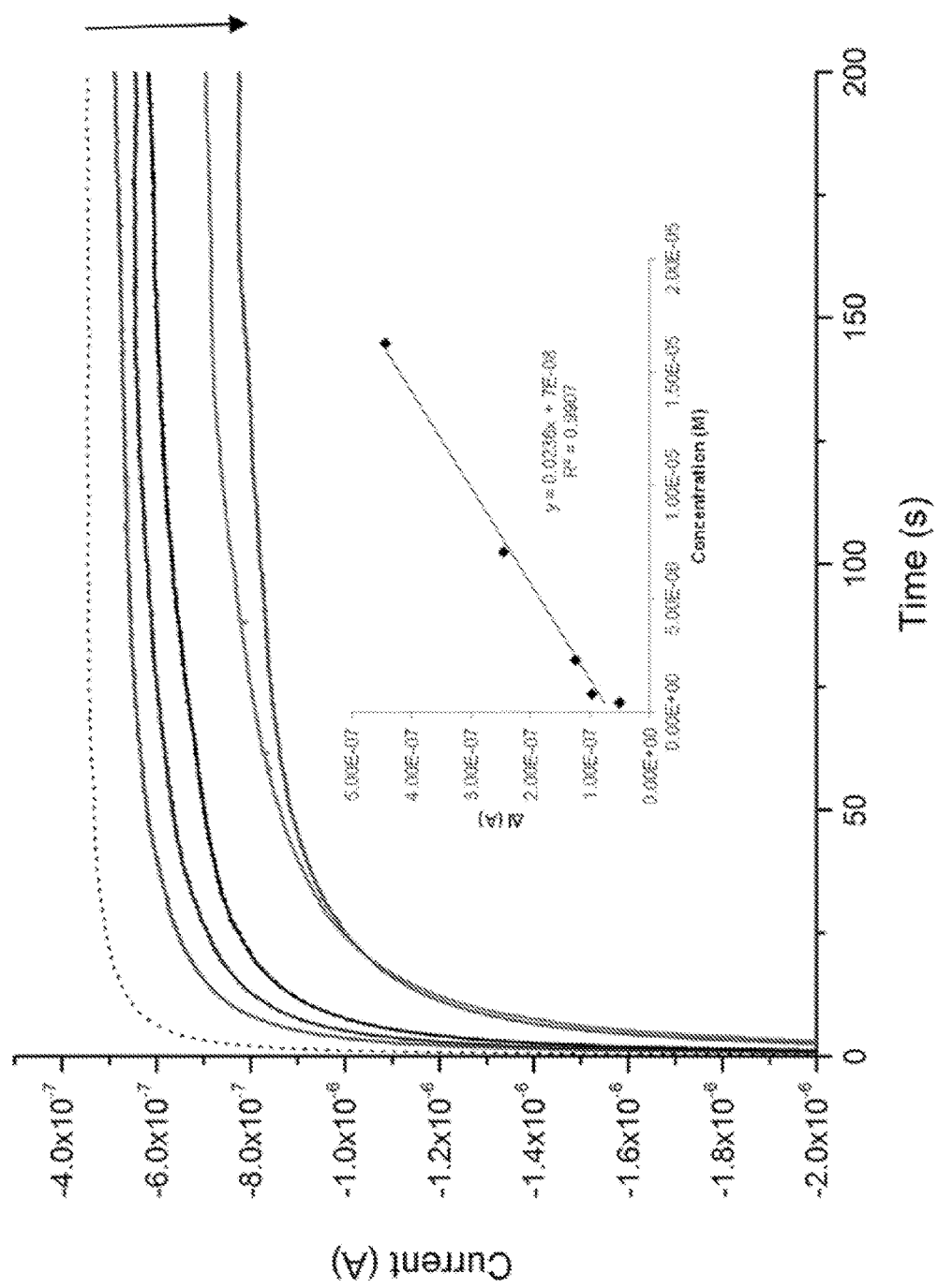
FIG. 5 shows a data plot of the chronoamperometric response of an exemplary electrochemical sensor of the disclosed technology exposed to increasing L-DOPA concentrations in PBS.

FIG. 5 shows a data plot of the chronoamperometric response of an exemplary electrochemical sensor of the disclosed technology exposed to increasing L-DOPA concentrations (e.g., 0.4, 0.8, 2.3, 7, 16 µM) in PBS, in which the dotted line corresponds to the blank solution. A corresponding calibration curve is shown in the insert of FIG. 5.

Figure 6A:
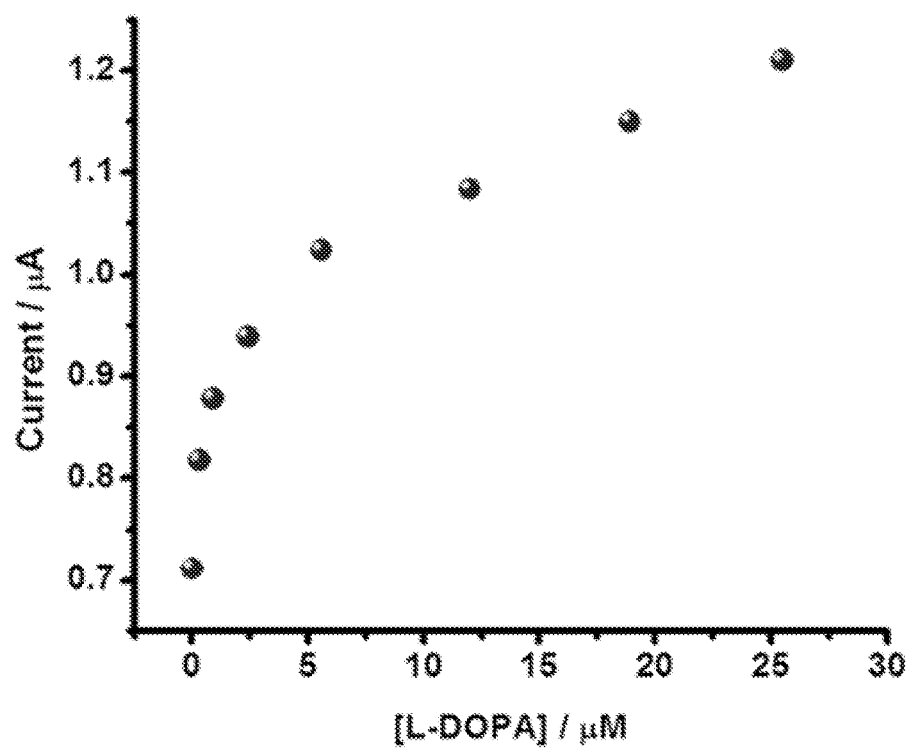
FIGS. 6A and 6B show data plots of the calibration curve for L-DOPA detection and the chronoamperometric response to increasing L-DOPA concentrations in buffer solution.
Figure 6B:
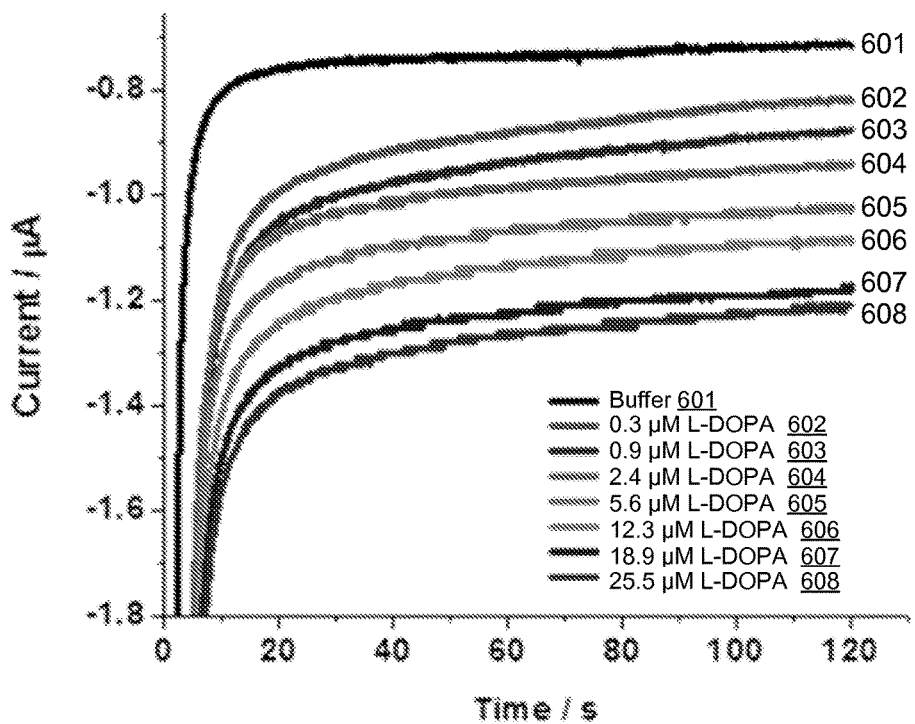

FIG. 6A shows a data plot of the calibration curve for L-DOPA detection, and FIG. 6B shows the chronoamperometric response, to increasing L-DOPA concentrations (e.g., 0, 0.3, 0.9, 2.4, 5.6, 12.3, 18.9 and 25.5 µM) in PBS. The data curves 601, 602, 603, 604, 605, 606, 607, and 608 in FIG. 6B correspond to the chronoamperometric responses for the PBS buffer only, and 0.3, 0.9, 2.4, 5.6, 12.3, 18.9 and 25.5 µM L-DOPA concentrations in PBS, respectively. As shown in the exemplary results featured in the data plots, the exemplary electrochemical sensor exhibited a typical Michaels-Menten behavior with a logarithmic correlation current/L-DOPA concentration.

Figure 7:
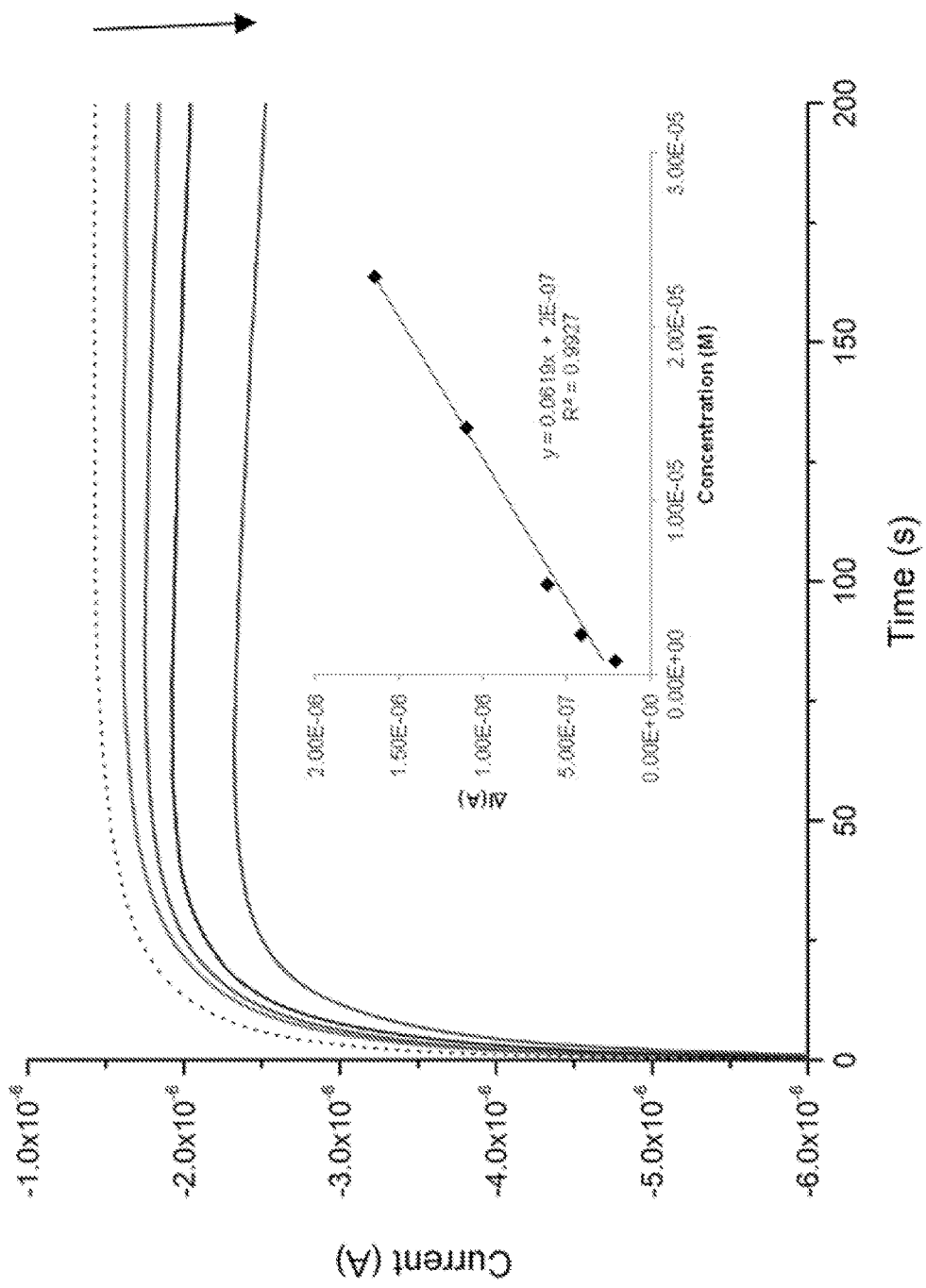
FIG. 7 shows a data plot of the chronoamperometric response of an exemplary electrochemical sensor of the disclosed technology exposed to a serum sample spiked with increasing L-DOPA concentrations.

The applicability of the sensor in serum samples was evaluated in these exemplary implementations by using a CNT/polythionine/tyrosinase/Nafion sensor. For example, the Nafion-coated sensors provided a slightly different concentration range (e.g., 0.8-22.3 µM) than that achieved in PBS solutions, as shown in FIG. 7 depicting the chronoamperometric response of the sensor exposed to increasing L-DOPA concentrations and the corresponding calibration curve. FIG. 7 shows a data plot of the chronoamperometric response of an exemplary sensor exposed to a serum sample spiked with increasing L-DOPA concentrations (e.g., 0.8, 2.3, 5.2, 14, 22.3 µM) in which the dotted line corresponds to the unspiked serum sample. A corresponding calibration curve is shown in the insert.

The disclosed methods, systems, and devices include disposable electrochemical sensors that can be used for the determination of targeted analytes such as L-DOPA directly in physiological fluids. As shown by the exemplary implementations, the presence of CNTs increased the sensor sensitivity and the tyrosinase immobilization onto the poly (thionine) layer are highly effective and advantageous for targeted selectivity. For example, some advantages of the disclosed technology include, but are not limited to, no requirement for sample pre-treatment, disposability of the sensor (mitigating poisoning or decreased sensitivity from repeated reuse), the low cost and small instrumental arrangement (working, auxiliary and reference electrodes are all confined in a very little area) of the screen printed electrodes used as support, and others, which encourage its use in clinical analysis.

In some aspects of the disclosed electrochemical sensor technology, a portable system to detect and quantitatively analyze a target analyte in a physiological fluid, e.g., such as blood, serum, plasma, saliva, and/or interstitial fluid includes a disposable electrochemical test strip sensor, which can include the electrochemical sensor 100 or 110, and a hand-held electrochemical analyzer device to operate an electrochemical analysis technique when the test strip sensor is inserted into the electrochemical analyzer device having a sample of the physiological fluid over the electrodes. For example, the disposable electrochemical test strip sensor can include a substrate formed of an insulative material, an electrode contingent including a first electrode having a coating of carbon nanotubes (CNTs) and a second electrode on the substrate, an entrapment layer including a conductive polymer film on the first electrode to attach an enzymatic substance capable of catalyzing a target analyte of a physiological fluid sample, and first and second contact pads on the substrate that are respectively electrically coupled to the first and the second electrodes via electrically conductive conduits. The electrochemical analyzer can include a housing including an opening to receive the disposable electrochemical test strip sensor, and an electrical circuit including bonding pads disposed in the opening to electrically couple to the electrochemical test strip sensor via first and the second contact pads when the electrochemical test strip sensor is inserted into the opening, in which the electrical circuit is operable to supply an electrical waveform to the electrochemical test strip sensor to operate an electrochemical analysis technique and to detect electrical signals transduced by the first and second electrodes during the electrochemical analysis technique. The enzymatic substance is provided by the electrochemical sensor to cause a redox reaction involving the target analyte when the physiological fluid sample is deposited on the electrodes that produces charge carriers associated with the redox reaction capable of being electrically conducted across the conductive polymer film and detectable at the first electrode by the electrical circuit.

Figure 8A:
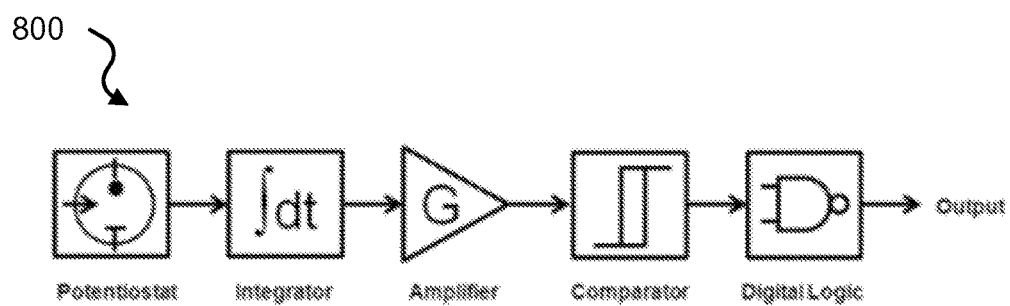
FIG. 8A shows a block diagram depicting an exemplary electrical circuit in a hand-held electrochemical analyzer device of the disclosed technology.
Figure 8A:
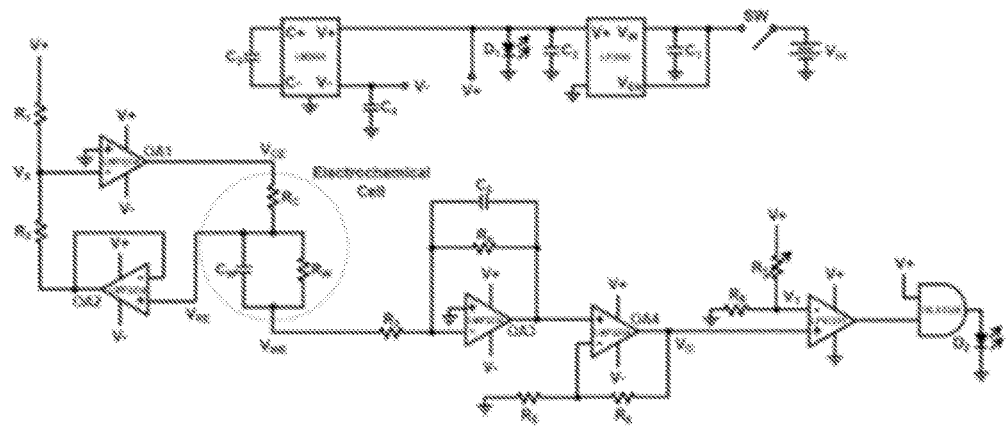

FIG. 8A shows a circuit diagram of an exemplary handheld electrochemical analyzer device including an electrical circuit 800 to analyze the detected signals. The handheld electrochemical analyzer device can also include a data processing and wireless communications unit in communication with the electrical circuit 800. For example, in some implementations, the components of the electrochemical analyzer can include a precision amperometric analog front end (AFE) hardware to generate a current response that exhibits proportionality to the concentration of the analyte in the physiological fluid sample on the electrodes of the test strip sensor (e.g., L-DOPA in whole blood, in correspondence with Cottrell's equation). The construction of this exemplary potentiostat can include a suitable electronic feedback network (as shown in the diagram of FIG. 8A) capable of highly-precise current response in conjunction with the application of a stable reference potential regardless of the conductivity of the sample. For example, a high-gain, low-noise AFE can be instituted in the electrochemical analyzer device, e.g., via a high input impedance (e.g., >100 TΩ) CMOS-based instrumentation amplifier contingent to provide that sub-nanoampere-level currents arising from low target concentrations (i.e., pg/mL) can be quantified with a high degree of accuracy. A filtering scheme to mitigate noise is instituted in the AFE including a high-resolution analog-to-digital converter (e.g., >14 bit) to quantize the acquired signal with high precision. The AFE can include electromagnetic shielding and ultra-sensitive components, e.g., ultra-low bias current instrumentation amplifiers.

FIG. 8A shows a block diagram depicting the functional behavior of exemplary amperometric analog front end hardware of an exemplary electrical circuit in a hand-held electrochemical analyzer device and a circuit-level schematic of supporting electronics for implementation of an electrochemical analysis technique (e.g., amperometric assay) using the exemplary hand-held electrochemical analyzer device.

For example, in some implementations, the data processing unit of the electrochemical analyzer can include a processor (e.g., a microcontroller). For example, a low-power programmable microcontroller (MCU) enables loading the handheld device with application-specific custom firmware containing analyte test algorithms and control commands for all components of the device. For example, any requirements for proper sensor operation are also written in the firmware, including but not limited to, drive voltages for the electrochemical reaction, the method of measurement (one time, real-time, time delay, time average, etc.), variables for temperature compensation, and calibration data. In one exemplary implementation, the data processing unit includes a highly-efficient 8-bit AVR-based MCU and contains an embedded potentiostatic firmware designed to execute the pre-programmed amperometric routines (control the potentiostat) and route digitized readings to the wireless transceiver module for transmission. The MCU can also be programmed to execute a suite of signal-processing algorithms to maximize signal-to-noise ratio as well as an auto-calibration routine.

For example, in some implementations, the wireless communication unit of the electrochemical analyzer can include a transmitter/receiver (transceiver), e.g., Bluetooth® Low Energy Radio (BLE). For example, a BLE transceiver module can be embedded in the analyzer to facilitate the ultra-low-power transmission of readings to a local mobile communication device, e.g., such as a smartphone, tablet, wearable communication device, or personal computer. For example, from there, records can be sent to a secure database for archiving and review, in which all readings will be secured during transmission using a HIPPA-compliant 128-bit AES encryption protocol.

For example, in some implementations, the wireless communication unit of the electrochemical analyzer can include peripheral devices, e.g., such as a power supply, a display, and/or user interface components. For example, to relay the quantified analyte data reading to the user, a large, easy-to-read backlit liquid crystal display (LCD) can be employed on the exemplary handheld electrochemical analyzer device to provide immediate visual data and feedback regarding operation of the device. The device can also feature a rechargeable lithium-polymer battery, a micro-USB port to charge the device and streamline firmware updates, and a single pushbutton switch to reset the device, activate it from the "off" state, and respond to notifications generated by the device.

For example, in some implementations, the wireless communication unit of the electrochemical analyzer can include a printed circuit board (PCB) possessing dimensions of less than 5 cm×10 cm (handheld form factor) to fit in the housing. The device can be flashed with the latest firmware and assigned a unique hardware identifier. The PCB can be embedded in a low-profile rubberized enclosure to ruggedize the unit for clinical use.

Figure 8B:
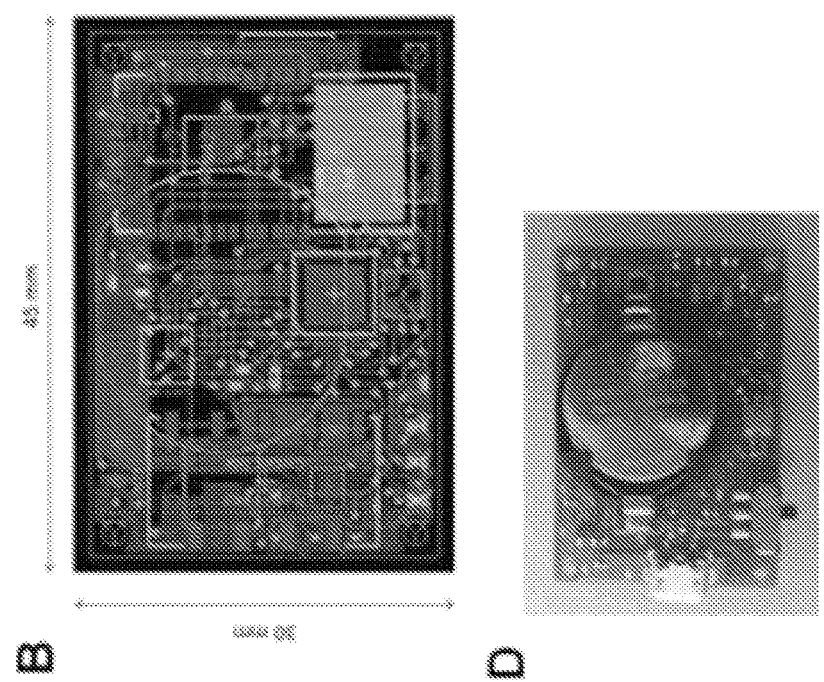
FIG. 8B shows a panel of diagrams and images depicting an exemplary data processing unit of the exemplary handheld electrochemical analyzer.
Figure 8B:
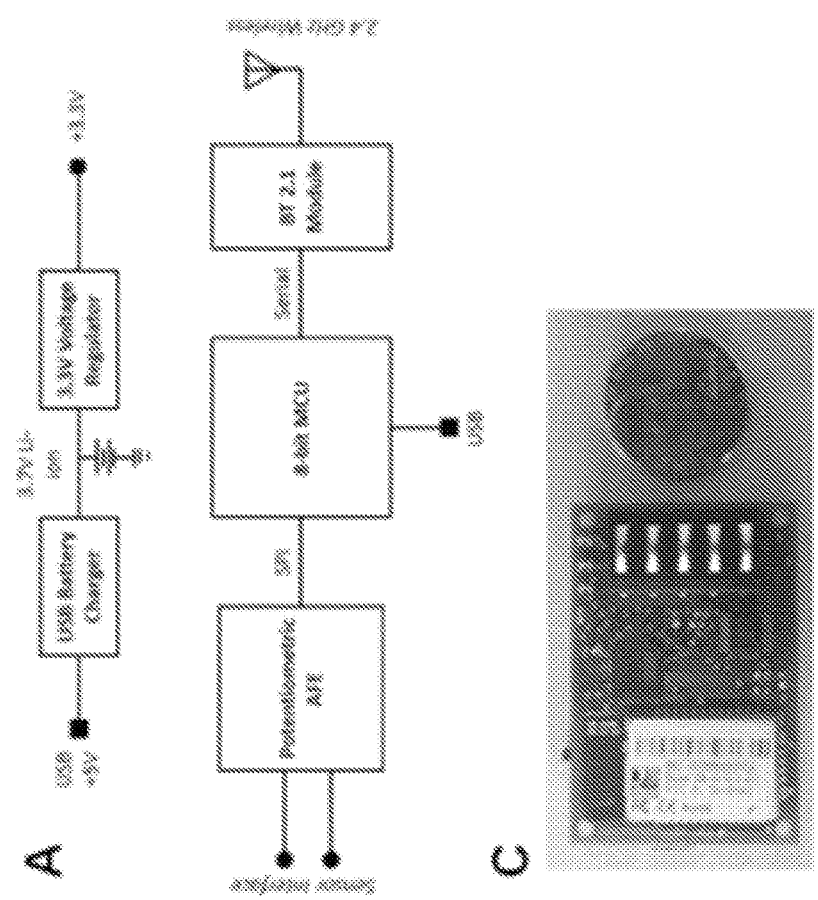

FIG. 8B shows a panel of diagrams and images depicting an exemplary data processing unit of the exemplary handheld electrochemical analyzer. FIG. 8B panel (A) shows a block-level diagram of sub-systems employed in an exemplary low-power, wireless electrochemical analyzer of the disclosed technology. FIG. 8B panel (B) shows a circuit-level layout of the exemplary components used in an example embodiment of the handheld electrochemical analyzer device with dimensions (e.g., 30 mm×45 mm) shown. FIG. 8B panels (C) and (D) respectively show the obverse and reverse of the printed circuit board-mounted analyzer illustrating the compact nature of the instrumentation (in which a US 5¢ coin is shown for scale). A rechargeable coin-cell battery is integrated on the reverse of the PCB while a Bluetooth v2.1 module is found on the obverse.

In operations of the exemplary handheld electrochemical analyzer device, a user obtains a fingerstick blood sample and inserts the test strip into a zero insertion force connector mounted on the PCB via an opening in the housing. Upon insertion of the test strip, the handheld analyzer immediately activates, performs the electrochemical analysis, tenders the results, and can store past values in local memory in the absence of user intervention. The reading (with a timestamp) can easily be transmitted to the local mobile device or exported to a centralized secure repository for safekeeping at the push of a button. Upon removal of the test strip, the device can power off such that it will only activate upon insertion of another strip (with sample).

L-DOPA

L-DOPA (L-3,4-dihydroxyphenylalanine) is a biochemical agent that is naturally synthesized in the nervous system from the amino acid L-tyrosine and serves as the precursor to the neurotransmitters dopamine, norepinephrine, and epinephrine, collectively known as catecholamines. LDOPA freely traverses the protective blood-brain barrier, whereas the catecholamine neurotransmitters themselves cannot. Thus, oral L-DOPA supplements (levodopa) are widely used to increase dopamine concentrations in the treatment of Parkinson's disease (PD) and dopamineresponsive dystonia. The administration of levodopa (and carbidopa) therapies is highly individualized and must be dosed in accordance with the control of symptoms, which are highly variable among individuals; hence there is no "standard dose" of levodopa. Moreover, during the course of treatment, it is often the case that, to maintain the same therapeutic effect, the levels of L-DOPA must be gradually increased as treatment ensues whereas the threshold for side-effects, e.g., such as dyskinesia, deterioration of fine motor function, anxiety attacks, and freezing during movement, resulting in a narrowing window of therapeutic effectiveness for a given dose. For example, currently, a PD patient must return to the healthcare provider on a frequent basis to evaluate the therapy's effectiveness and adjust the dosing for proper control of the disease. Surprisingly, this evaluation is performed via a visual assessment of fine motor control and patient testimony on frequency and severity of tremors and, in very rare cases, a blood sample is sent to a centralized laboratory for L-DOPA quantification, a costly proposition that typically requires a 2-3-week turnaround time.

Despite continuing advances in the treatment of PD, levodopa remains the therapeutic agent of choice throughout the course of the disease and levodopa-mitigated symptom relief is better tolerated than dopamine agonists, but as proteins compete with levodopa absorption, patients must adhere to challenging schedules to avoid consuming this medication with meals. This further obfuscates the management of PD on behalf of both the patient and healthcare provider. Surprisingly, current management of levodopa is still based on a patient's report of clinical symptoms rather than on evidence-based knowledge of its blood levels. However, if a simple method to determine the blood levels of levodopa did exist, it would allow patients and their neurologists to better understand the variable levodopa motor and non-motor response and better adjust individual doses, which, in turn, would significantly improve the management of PD symptoms.

Accordingly, a cost-effective, easy-to-perform technique and platform is needed to provide individualized feedback on a proper levodopa/carbidopa dosing regimen in a decentralized and rapid fashion. The disclosed electrochemical sensor devices, systems, and methods can provide low cost, robust, decentralized (e.g. portable), and accurate quantitative analysis of targeted analytes in physiological fluid samples such as L-DOPA over physiological and pathological ranges.

The exemplary disposable levodopa test strip electrochemical sensors of the disclosed technology enable fingerstick blood sampling and analysis intended to cause a paradigm shift by allowing patients and physicians to better manage PD by dynamically adjusting levodopa doses based on real-time blood levels. This, in turn, would improve patients' and caregivers' quality of life and decrease healthcare costs by reducing the need for frequent visits to the point-of-care for dosing adjustment, thereby alleviating the burden on the healthcare provider. Specifically, this would have substantial implications for PD patients with fluctuations in their response to levodopa and those experiencing a lack of benefit from individualized doses. Since continuously infused and properly dosed levodopa can prevent dyskinesia and lead to reduced disability, surgery can possibly be delayed using this approach.

The disclosed technology provides the capability to identify the proper levodopa dosing regimen via the exemplary LDOPA-selective disposable test strip sensors that can be analyzed using a handheld electrochemical analyzer. The exemplary handheld electrochemical analyzer device of the disclosed technology can provide users with a real-time profile of circulating LDOPA levels in a minimally-invasive fashion, thereby leading to substantially improved clinical outcomes among those afflicted with PD. This paradigm enables the individual to take proactive measures to assess their proper levodopa dosing regimen throughout their daily routine, thereby mitigating the likelihood of hospital admission due to side effects such as dyskinesias and severe gait disturbances such as freezing during movement, leading to falls and fractures. In addition to providing real-time feedback to the patient, the exemplary systems can leverage the wireless infrastructure to relay the data to the healthcare provider for review, trending, and archiving. Accordingly, this capability can substantially improve the manner in which PD is managed, thereby improving outcomes, while simultaneously reducing healthcare costs and alleviating the burden on the healthcare provider. The disclosed technology provides advantageous features, e.g., including high sensitivity, stability, selectivity, simplicity, versatility, and robustness at a price that is amenable to widespread healthcare adoption.

In an example operation of the exemplary system (e.g., an exemplary LDOPA-selective disposable test strip sensor and an exemplary handheld electrochemical analyzer), a user employs a lancet or other skin-piercing device to access a small blood sample. Among other locations, this blood sample can be taken from the fingertip, hand, arm, deltoid, abdomen, or ear lobe. The electrochemical test strip sensor (e.g., such as the sensor 100 or 110 or other examples described above) can include screen printed working, reference, and counter electrodes, on which the physiological sample (e.g. blood) is then placed in contact (e.g., such as touching the pricked blood to the test strip body for wicking to the electrode contingent). In operation, a chemical reaction ensues whereby the tyrosinase biocatalytically oxidizes L-DOPA to dopaquinone while simultaneously reducing free oxygen to form water, as shown previously in FIG. 2B. In the presence of dopaquinone, the poly(thionine) film on the working electrode is oxidized, which concomitantly serves to reduce dopaquinone back to L-DOPA.

To operate the exemplary handheld electrochemcial analyzer, for example, the electrochemical test strip described above is inserted into a zero-insertion force connector on the bottom side of the handheld analyzer following a fingerstick blood sample. Subsequently, a small electrical potential is applied at the working electrode (with respect to the reference electrode), e.g., using an amperometric electrochemical analysis technique. In a two-electron transfer process, the oxidized poly(thionine) present on the electrode (resulting from the chemical oxidation of poly(thionine) imparted by the presence of dopaquinone) is converted to a reduced form of poly(thionine). The magnitude of this electron flow (between the working electrode and counter electrode or vice versa), e.g., the electrical current, is regulated by the chemical reaction (specifically the amount of reactant, L-DOPA) and is measured using the potentiostat. By merit of electrochemical principles, e.g., namely the Cottrell equation, the magnitude of the current measured with respect to time will be proportional to the concentration of the analyte (in this case L-DOPA) in the blood sample. The value measured for the electrical current can be inserted into a calibration equation or compared to a calibration table to determine the L-DOPA concentration corresponding to this reading.

EXAMPLES

The following examples are illustrative of several embodiments of the present technology. Other exemplary embodiments of the present technology may be presented prior to the following listed examples, or after the following listed examples.

In an example of the present technology (example 1), an electrochemical sensor includes a substrate formed of an insulative material; an electrode contingent including a first electrode and a second electrode on the substrate, in which the first electrode includes a coating of carbon nanotubes (CNTs); and an entrapment layer formed on the first electrode to attach an enzymatic substance capable of causing a redox reaction in the presence of a target analyte of a fluid sample which produces a redox-active product, in which the entrapment layer is structured to include a conductive polymer film that is reversibly dopable to conduct charge carriers across the entrapment layer and at the first electrode.

Example 2 includes the electrochemical sensor of example 1, in which the electrochemical sensor is operable for electrochemical analysis of a fluid sample when the fluid sample is in contact with the electrode contingent, and when the electrochemical sensor is electrically coupled to an electrical circuit to supply an electrical waveform to the electrode contingent to transduce chemical information associated with the target analyte that is present in the fluid sample to an electrical signal.

Example 3 includes the electrochemical sensor of example 2, in which the electrical signal indicates a concentration level of the target analyte in the fluid sample.

Example 4 includes the electrochemical sensor of example 3, in which the magnitude of the electrical signal with respect to time changes in proportion to the concentration of the target analyte.

Example 5 includes the electrochemical sensor of example 1, in which the electrochemical sensor is formed on a disposable test strip.

Example 6 includes the electrochemical sensor of example 5, further including electrode interface contacts on the substrate that are electrically coupled to the electrodes via electrically conductive conduits, in which the electrode interface contacts are operable to provide electrical signals detected by the electrode contingent when the disposable electrochemical test strip sensor is electrically interfaced with an electrochemical analyzer device.

Example 7 includes the electrochemical sensor of example 6, further including an electrically insulative cover layer at least partially formed over the electrically conductive conduits.

Example 8 includes the electrochemical sensor of example 1, in which the coating of CNTs includes single-walled carbon nanotubes (SWCNTs), multi-walled carbon nanotubes (MWCNTs), or a combination of SWCNTs and MWCNTs.

Example 9 includes the electrochemical sensor of example 1, in which the first electrode is operable as a working electrode, and the second electrode is operable as a counter electrode and/or a reference electrode in an electrochemical analysis technique.

Example 10 includes the electrochemical sensor of example 9, in which the first electrode includes carbon, platinum, palladium, rhodium, iridium, nickel, or gold, and the second electrode is an Ag/AgCl electrode.

Example 11 includes the electrochemical sensor of example 1, in which the electrode contingent includes a third electrode, and the first electrode is operable as a working electrode, and the second electrode is operable as a counter electrode, and the third electrode is operable as a reference electrode in an electrochemical analysis technique.

Example 12 includes the electrochemical sensor of example 11, in which the first and the second electrodes include carbon, the third electrode is an Ag/AgCl electrode.

Example 13 includes the electrochemical sensor of example 1, in which the conductive polymer film includes poly(thionine).

Example 14 includes the electrochemical sensor of example 1, in which the enzymatic substance includes tyrosinase, catechol oxidase, polyphenol oxidase, or monophenol monooxygenase, or a combination thereof.

Example 15 includes the electrochemical sensor of example 1, in which the conductive polymer film is cross-linked to the enzymatic substance using a solution containing bovine serum albumin, glutaraldehyde, and the enzymatic substance.

Example 16 includes the electrochemical sensor of example 1, further including a protective layer over the entrapment layer on the first electrode, in which the protective layer includes a charge-exclusion material that allows charge neutral species and either positively or negatively charged species to pass through the protective layer.

Example 17 includes the electrochemical sensor of example 16, in which the protective layer includes a Nafion film, in which the protective layer prohibits negatively charged chemical species from passing through the protective layer.

Example 18 includes the electrochemical sensor of example 16, in which the protective layer is formed over all of the electrodes of the electrode contingent.

Example 19 includes the electrochemical sensor of example 1, in which the fluid sample includes a physiological fluid sample including blood, plasma, serum, saliva, or interstitial fluid samples.

Example 20 includes the electrochemical sensor of example 1, in which the conductive polymer film includes poly(thionine), the enzymatic substance includes tyrosinase, and the target analyte includes L-DOPA in the fluid sample including whole blood, serum, or plasma, such that the electrochemical sensor is operable to detect the electrical signals associated with the concentration of the L-DOPA in the fluid sample when the electrochemical sensor is electrically coupled to an electrical circuit, by which the tyrosinase is capable to biocatalytically oxidize the L-DOPA to dopaquinone at the first electrode, such that the presence of dopaquinone causes the poly(thionine) film at the first electrode to oxidize, which concomitantly causes the dopaquinone to reduce back to L-DOPA.

In an example of the present technology (example 21), a method to produce an analyte-selective electrochemical sensor includes providing a signal sensitivity-enhanced electrode on a substrate of an electrochemical sensor including carbon nanotubes (CNTs) on the surface of the electrode; forming an entrapment layer over the signal sensitivity-enhanced electrode by depositing a solution of a polymer material on the surface of the electrode, and applying a fixed potential at the electrode and, subsequently, a continuously-cycled potential with respect to a reference electrode to produce a reversibly dopable conducting polymer film on the electrode; and attaching an enzymatic substance to the entrapment layer by depositing a solution containing the enzymatic substance, an enzyme stabilizing agent, and a cross-linking agent on the conducting polymer film and drying the solution.

Example 22 includes the method of example 21, in which the providing the signal sensitivity-enhanced electrode includes depositing a dispersed solution including the CNTs on the surface of a formed electrode on the substrate, and drying the solution to produce a layer of the CNTs.

Example 23 includes the method of example 21, in which the providing the signal sensitivity-enhanced electrode includes forming a carbon-based screen printed electrode using a conductive ink material that contains the CNTs within the ink.

Example 24 includes the method of example 21, in which the enzymatic substance is capable of catalyzing a target analyte of a fluid sample to cause a redox reaction detectable at the electrode when using an electrochemical analysis technique to operate the electrochemical sensor.

Example 25 includes the method of example 21, in which the polymer material to form the conductive polymer film includes poly(thionine).

Example 26 includes the method of example 21, in which the enzymatic substance includes tyrosinase, catechol oxidase, polyphenol oxidase, or monophenol monooxygenase, or a combination thereof.

Example 27 includes the method of example 21, in which the enzyme stabilizing agent includes bovine serum albumin, and in which the cross-linking agent includes glutaraldehyde.

Example 28 includes the method of example 21, further including producing a charge exclusion layer by depositing a solution containing Nafion and drying the solution.

Example 29 includes the method of example 28, in which the depositing the charge-exclusion solution and drying is repeated multiple times.

Example 30 includes the method of example 21, in which the electrochemical sensor is formed on a test strip.

Example 31 includes the method of example 21, further including storing the electrochemical sensor for future use.

In an example of the present technology (example 32), a system to detect an analyte in a physiological sample includes a disposable electrochemical test strip sensor structured to include a substrate formed of an insulative material, an electrode contingent including a first electrode having a coating of carbon nanotubes (CNTs) and a second electrode on the substrate, an entrapment layer including a conductive polymer film on the first electrode to attach an enzymatic substance capable of catalyzing a target analyte of a physiological fluid sample, and first and second contact pads on the substrate that are respectively electrically coupled to the first and the second electrodes via electrically conductive conduits; and a portable electrochemical analyzer including a housing including an opening to receive the disposable electrochemical test strip sensor, and an electrical circuit including bonding pads disposed in the opening to electrically couple to the electrochemical test strip sensor via first and the second contact pads when the electrochemical test strip sensor is inserted into the opening, in which the electrical circuit is operable to supply an electrical waveform to the electrochemical test strip sensor to operate an electrochemical analysis technique and to detect electrical signals transduced by the first and second electrodes during the electrochemical analysis technique, in which the enzymatic substance is provided to cause a redox reaction involving the target analyte when the physiological fluid sample is deposited on the electrodes that produces charge carriers associated with the redox reaction capable of being electrically conducted across the conductive polymer film and detectable at the first electrode by the electrical circuit.

Example 33 includes the system of example 32, in which the portable electrochemical analyzer includes a signal conditioning circuit to amplify the detected electrical signals by the first electrode.

Example 34 includes the system of example 33, in which the portable electrochemical analyzer includes a data processing unit including a processor to process data based on the detected electrical signal and a memory to store or buffer the data.

Example 35 includes the system of example 32, in which the portable electrochemical analyzer includes a wireless communications unit to wirelessly transmit the detected electrical signal to an external computing device including a smartphone, a tablet, a smartglasses, a smartwatch, a laptop computer, a desktop computer, or a network of computers in communication via the Internet.

In an example of the present technology (example A1), an electrochemical sensor includes a substrate formed of an insulative material; a plurality of electrodes of an electrically conductive material on the substrate, the electrodes including a working electrode, a counter electrode, and a reference electrode, in which the working electrode includes a coating formed of single- or multi-walled carbon nanotubes (CNTs); and electrode interface contacts on the substrate and electrically coupled to the electrodes via electrically conductive conduits, in which the electrochemical sensor is operable for electrochemical analysis of a sample when the sample is in physical contact with the working electrode and the electrochemical sensor is electrically coupled, via the electrode interface contacts, to an electrical circuit to transduce chemical information associated with one or more chemical agents in the sample based on an electrical signal.

Example A2 includes the electrochemical sensor of example A1, further including an electrically insulative cover layer at least partially formed over the electrically conductive conduits.

Example A3 includes the electrochemical sensor of example A1, in which the reference electrode is an Ag/AgCl electrode.

Example A4 includes the electrochemical sensor of example A1, in which the electrodes include an analyte detection layer including a polymer film that entraps an enzymatic substance capable of binding to a chemical agent target.

Example A5 includes the electrochemical sensor of example A4, in which the polymer film includes poly(thionine).

Example A6 includes the electrochemical sensor of example A4, in which the enzymatic substance includes at least one of enzyme tyrosinase, catechol oxidase, polyphenol oxidase, or monophenol monooxygenase.

Example A7 includes the electrochemical sensor of example A4, in which the enzymatic substance is cross-linked using a solution containing bovine serum albumin, glutaraldehyde, and the enzymatic substance.

Example A8 includes the electrochemical sensor of example A4, in which the electrodes includes a Nafion film over the outer surface (e.g., the working electrode surface).

Example A9 includes the electrochemical sensor of example A4, in which the chemical agent target includes L-DOPA and the sample includes whole blood, serum, plasma, interstitial fluid, and/or saliva, and in which the enzymatic substance biocatalytically oxidizes L-DOPA to dopaquinone on the working electrode, such that the presence of dopaquinone causes the poly(thionine) film on the working electrode to oxidize, which concomitantly causes the dopaquinone to reduce back to L-DOPA.

Example A10 includes the electrochemical sensor of example A4, in which the electrical signal indicates a change (e.g., redox change) in the analyte detection layer.

Example A11 includes the electrochemical sensor of example A10, in which the magnitude of the electrical signal with respect to time changes in proportion to the concentration of the chemical agent target.

Example A12 includes the electrochemical sensor of example A1, in which the electrochemical sensor is formed on a strip.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An electrochemical sensor, comprising:
   a substrate formed of an insulative material;
   an electrode contingent including a first electrode and a second electrode on the substrate, wherein the first electrode includes a coating of carbon nanotubes (CNTs); and
   an entrapment layer formed on the first electrode to attach an enzymatic substance capable of causing a redox reaction in the presence of a target analyte of a fluid sample which produces a redox-active product, wherein the entrapment layer is structured to include a conductive polymer film that is reversibly dopable to conduct charge carriers across the entrapment layer and at the first electrode,
   wherein the conductive polymer film includes poly(thionine).

2. The electrochemical sensor of claim 1, wherein the electrochemical sensor is operable for electrochemical analysis of a fluid sample when the fluid sample is in contact with the electrode contingent and the electrochemical sensor is electrically coupled to an electrical circuit to supply an electrical waveform to the electrode contingent to transduce chemical information associated with the target analyte that is present in the fluid sample to an electrical signal.

3. The electrochemical sensor of claim 2, wherein the electrical signal indicates a concentration level of the target analyte in the fluid sample.

4. The electrochemical sensor of claim 3, wherein the magnitude of the electrical signal with respect to time changes in proportion to the concentration of the target analyte.

5. The electrochemical sensor of claim 1, wherein the electrochemical sensor is formed on a disposable test strip.

6. The electrochemical sensor of claim 5, further comprising electrode interface contacts on the substrate that are electrically coupled to the electrodes via electrically conductive conduits, wherein the electrode interface contacts are operable to provide electrical signals detected by the electrode contingent when the disposable electrochemical test strip sensor is electrically interfaced with an electrochemical analyzer device.

7. The electrochemical sensor of claim 6, further comprising an electrically insulative cover layer at least partially formed over the electrically conductive conduits.

8. The electrochemical sensor of claim 1, wherein the coating of CNTs includes single-walled carbon nanotubes (SWCNTs), multi-walled carbon nanotubes (MWCNTs), or a combination of SWCNTs and MWCNTs.

9. The electrochemical sensor of claim 1, wherein the first electrode is operable as a working electrode, and the second electrode is operable as a counter electrode and/or a reference electrode in an electrochemical analysis technique.

10. The electrochemical sensor of claim 9, wherein the first electrode includes carbon, platinum, palladium, rhodium, iridium, nickel, or gold, and the second electrode is an Ag/AgCl electrode.

11. The electrochemical sensor of claim 1, wherein the electrode contingent includes a third electrode, and the first electrode is operable as a working electrode, and the second electrode is operable as a counter electrode, and the third electrode is operable as a reference electrode in an electrochemical analysis technique.

12. The electrochemical sensor of claim 11, wherein the first and the second electrodes include carbon, the third electrode is an Ag/AgCl electrode.

13. The electrochemical sensor of claim 1, wherein the enzymatic substance includes tyrosinase, catechol oxidase, polyphenol oxidase, or monophenol monooxygenase, or a combination thereof.

14. The electrochemical sensor of claim 1, wherein the conductive polymer film is cross-linked to the enzymatic substance using a solution containing bovine serum albumin, glutaraldehyde, and the enzymatic substance.

15. The electrochemical sensor of claim 1, further comprising a protective layer over the entrapment layer on the first electrode, wherein the protective layer includes a charge-exclusion material that allows charge neutral species and either positively or negatively charged species to pass through the protective layer.

16. The electrochemical sensor of claim 15, wherein the protective layer includes a Nafion film, wherein the protective layer prohibits negatively charged chemical species from passing through the protective layer.

17. The electrochemical sensor of claim 15, wherein the protective layer is formed over all of the electrodes of the electrode contingent.

18. The electrochemical sensor of claim 1, wherein the fluid sample includes a physiological fluid sample including blood, plasma, serum, saliva, or interstitial fluid samples.

19. The electrochemical sensor of claim 1, wherein the conductive polymer film includes poly(thionine), the enzymatic substance includes tyrosinase, and the target analyte includes L-DOPA in the fluid sample including whole blood, serum, or plasma, such that the electrochemical sensor is operable to detect the electrical signals associated with the concentration of the L-DOPA in the fluid sample when the electrochemical sensor is electrically coupled to an electrical circuit, by which the tyrosinase is capable to biocatalytically oxidize the L-DOPA to dopaquinone at the first electrode, such that the presence of dopaquinone causes the poly (thionine) film at the first electrode to oxidize, which concomitantly causes the dopaquinone to reduce back to L-DOPA.

20. A method to produce an analyte-selective electrochemical sensor, comprising:
   providing a signal sensitivity-enhanced electrode on a substrate of an electrochemical sensor including carbon nanotubes (CNTs) on the surface of the electrode;
   forming an entrapment layer over the signal sensitivity-enhanced electrode by depositing a solution of a polymer material on the surface of the electrode, and applying a fixed potential at the electrode and, subsequently, a continuously-cycled potential with respect to a reference electrode to produce a reversibly dopable conducting polymer film on the electrode; and
   attaching an enzymatic substance to the entrapment layer by depositing a solution containing the enzymatic substance, an enzyme stabilizing agent, and a cross-linking agent on the conducting polymer film and drying the solution, wherein the polymer material to form the conductive polymer film includes poly(thionine).

21. The method of claim 20, wherein the providing the signal sensitivity-enhanced electrode includes depositing a dispersed solution including the CNTs on the surface of a formed electrode on the substrate, and drying the solution to produce a layer of the CNTs.

22. The method of claim 20, wherein the providing the signal sensitivity-enhanced electrode includes forming a carbon-based screen printed electrode using a conductive ink material that contains the CNTs within the ink.

23. The method of claim 20, wherein the enzymatic substance is capable of catalyzing a target analyte of a fluid sample to cause a redox reaction detectable at the electrode when using an electrochemical analysis technique to operate the electrochemical sensor.

24. The method of claim 20, wherein the enzymatic substance includes tyrosinase, catechol oxidase, polyphenol oxidase, or monophenol monooxygenase, or a combination thereof.

25. The method of claim 20, wherein the enzyme stabilizing agent includes bovine serum albumin, and wherein the cross-linking agent includes glutaraldehyde.

26. The method of claim 20, further comprising:
producing a charge exclusion layer by depositing a solution containing Nafion and drying the solution.

27. The method of claim 26, wherein the depositing the charge-exclusion solution and drying is repeated multiple times.

28. The method of claim 20, wherein the electrochemical sensor is formed on a test strip.

29. The method of claim 20, further comprising storing the electrochemical sensor for future use.

30. A system to detect an analyte in a physiological sample, comprising:
a disposable electrochemical test strip sensor structured to include a substrate formed of an insulative material, an electrode contingent including a first electrode having a coating of carbon nanotubes (CNTs) and a second electrode on the substrate, an entrapment layer including a conductive polymer film on the first electrode to attach an enzymatic substance capable of catalyzing a target analyte of a physiological fluid sample, and first and second contact pads on the substrate that are respectively electrically coupled to the first and the second electrodes via electrically conductive conduits; and a portable electrochemical analyzer including a housing including an opening to receive the disposable electrochemical test strip sensor, and an electrical circuit including bonding pads disposed in the opening to electrically couple to the electrochemical test strip sensor via first and the second contact pads when the electrochemical test strip sensor is inserted into the opening, wherein the electrical circuit is operable to supply an electrical waveform to the electrochemical test strip sensor to operate an electrochemical analysis technique and to detect electrical signals transduced by the first and second electrodes during the electrochemical analysis technique, wherein the enzymatic substance is provided to cause a redox reaction involving the target analyte when the physiological fluid sample is deposited on the electrodes that produces charge carriers associated with the redox reaction capable of being electrically conducted across the conductive polymer film and detectable at the first electrode by the electrical circuit, wherein the conductive polymer film includes poly(thionine).

31. The system of claim 30, wherein the portable electrochemical analyzer includes a signal conditioning circuit to amplify the detected electrical signals by the first electrode.

32. The system of claim 31, wherein the portable electrochemical analyzer includes a data processing unit including a processor to process data based on the detected electrical signal and a memory to store or buffer the data.

33. The system of claim 30, wherein the portable electrochemical analyzer includes a wireless communications unit to wirelessly transmit the detected electrical signal to an external computing device including a smartphone, a tablet, a pair of smartglasses, a smartwatch, a laptop computer, a desktop computer, or a network of computers in communication via the Internet.

* * * * *